(12) United States Patent
Sakurada et al.

(10) Patent No.: US 12,171,492 B2
(45) Date of Patent: Dec. 24, 2024

(54) OPHTHALMOLOGIC APPARATUS AND MEASUREMENT METHOD USING THE SAME

(71) Applicant: TOPCON CORPORATION, Tokyo (JP)

(72) Inventors: Tomohiro Sakurada, Tokyo (JP); Akira Mizuno, Tokyo (JP)

(73) Assignee: TOPCON CORPORATION, Tokyo (JP)

( * ) Notice: Subject to any disclaimer, the term of this patent is extended or adjusted under 35 U.S.C. 154(b) by 635 days.

(21) Appl. No.: 17/484,390

(22) Filed: Sep. 24, 2021

(65) Prior Publication Data

US 2022/0369921 A1    Nov. 24, 2022

Related U.S. Application Data

(60) Provisional application No. 63/191,575, filed on May 21, 2021.

(51) Int. Cl.
*A61B 3/00* (2006.01)
*A61B 3/028* (2006.01)

(52) U.S. Cl.
CPC .......... *A61B 3/0091* (2013.01); *A61B 3/0025* (2013.01); *A61B 3/0033* (2013.01); *A61B 3/0041* (2013.01); *A61B 3/0285* (2013.01)

(58) Field of Classification Search
CPC ... A61B 3/0091; A61B 3/0025; A61B 3/0033; A61B 3/0041; A61B 3/0285; A61B 3/103; A61B 3/032
USPC ....................................................... 351/237
See application file for complete search history.

(56) References Cited

U.S. PATENT DOCUMENTS

| 5,675,399 | A  | * | 10/1997 | Kohayakawa | ......... A61B 3/032 |
|           |    |   |         |            | 351/222 |
| 7,775,662 | B2 |   | 8/2010  | Kubota et al. | |
| 2005/0174534 | A1 | * | 8/2005 | Nakanishi | ............ A61B 3/0041 |
|           |    |   |         |            | 351/200 |
| 2005/0264760 | A1 |   | 12/2005 | Ikezawa | |

(Continued)

FOREIGN PATENT DOCUMENTS

EP      2 461 735      6/2012
JP      2004-283271    10/2004

(Continued)

OTHER PUBLICATIONS

Extended European Search Report issued Sep. 8, 2022 in European Patent Application No. 22163337.3.

(Continued)

*Primary Examiner* — Mohammed A Hasan
(74) *Attorney, Agent, or Firm* — Wenderoth, Lind & Ponack, L.L.P.

(57) ABSTRACT

An ophthalmologic apparatus includes a visual target projection system that is configured to present a visual target to a subject eye at under a presentation condition, and a controller. The controller is configured to control the visual target projection system to present the visual target at a first examination distance for a far-point examination of the subject eye, a second examination distance for a near-point examination of the subject eye, and a third examination distance that is different from the first examination distance and the second examination distance.

11 Claims, 17 Drawing Sheets

(56) References Cited

U.S. PATENT DOCUMENTS

| | | |
|---|---|---|
| 2011/0027766 A1 | 2/2011 | Yoo et al. |
| 2013/0201446 A1 | 8/2013 | Hall et al. |
| 2015/0342459 A1 | 12/2015 | Robert et al. |
| 2017/0181850 A1 | 6/2017 | de Juan, Jr. et al. |
| 2017/0245756 A1* | 8/2017 | Hayashi ................. A61B 3/107 |
| 2019/0223998 A1 | 7/2019 | de Juan, Jr. et al. |
| 2019/0282083 A1* | 9/2019 | Hayashi ................... A61B 3/12 |
| 2020/0085293 A1 | 3/2020 | Fujikado et al. |
| 2020/0201070 A1 | 6/2020 | Lerm et al. |
| 2021/0298599 A1* | 9/2021 | Takii .................... A61B 3/0025 |
| 2022/0192488 A1* | 6/2022 | Mino ..................... H04N 23/60 |

FOREIGN PATENT DOCUMENTS

| | | |
|---|---|---|
| JP | 2005-342042 | 12/2005 |
| JP | 2018-42761 | 3/2018 |
| JP | 2019-136569 | 8/2019 |
| JP | 2020-22762 | 2/2020 |
| WO | 2017/002846 | 1/2017 |
| WO | 2018/216551 | 11/2018 |

OTHER PUBLICATIONS

Office Action issued May 7, 2024 in Japanese Patent Application No. 2020-147847, with English translation.

\* cited by examiner

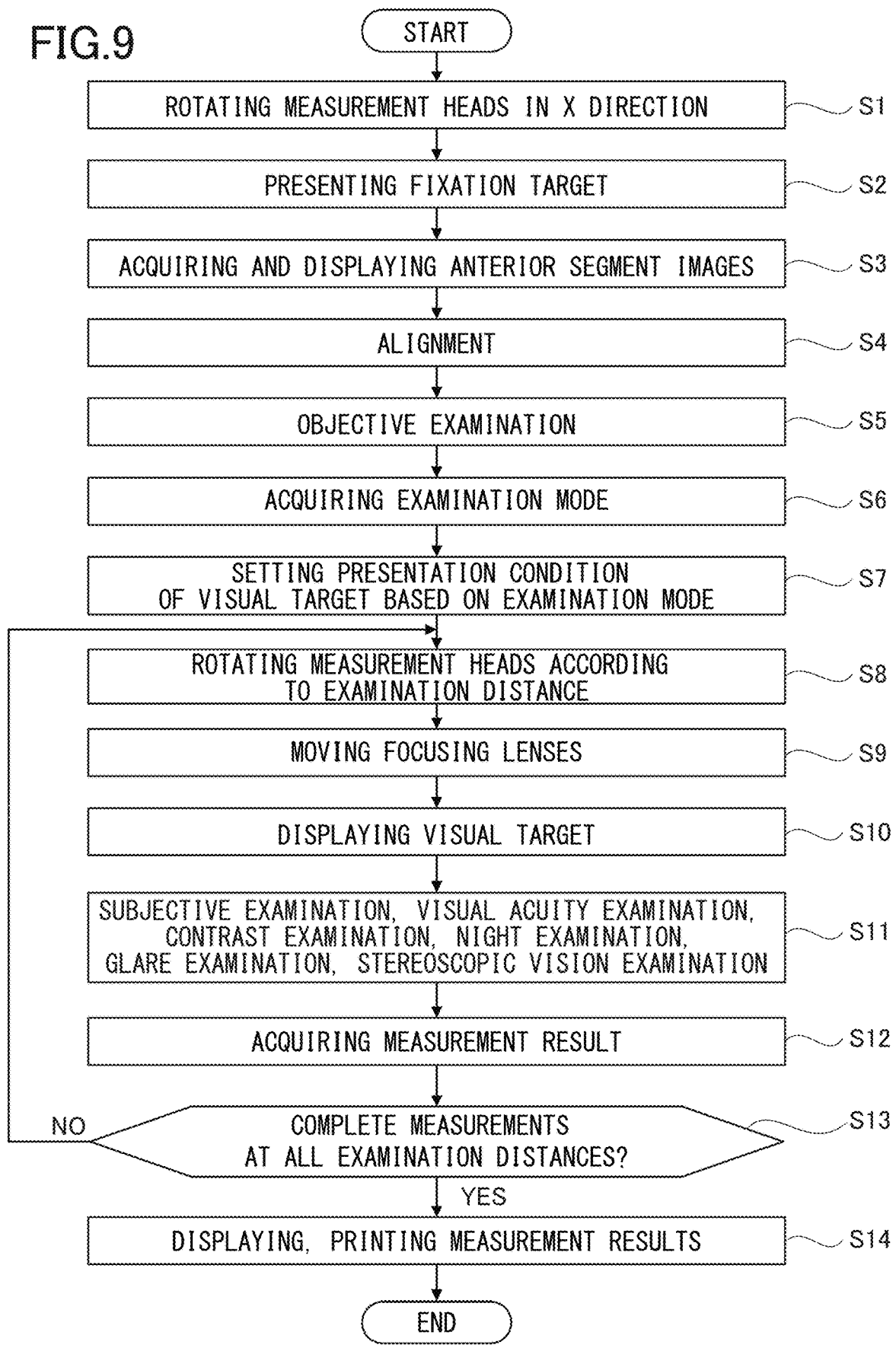

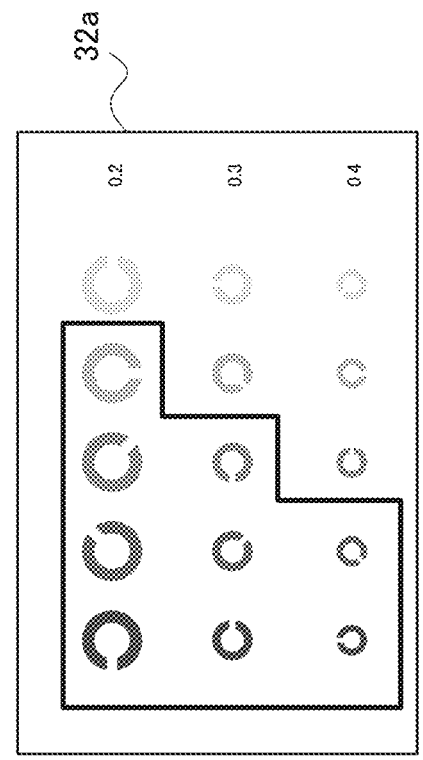
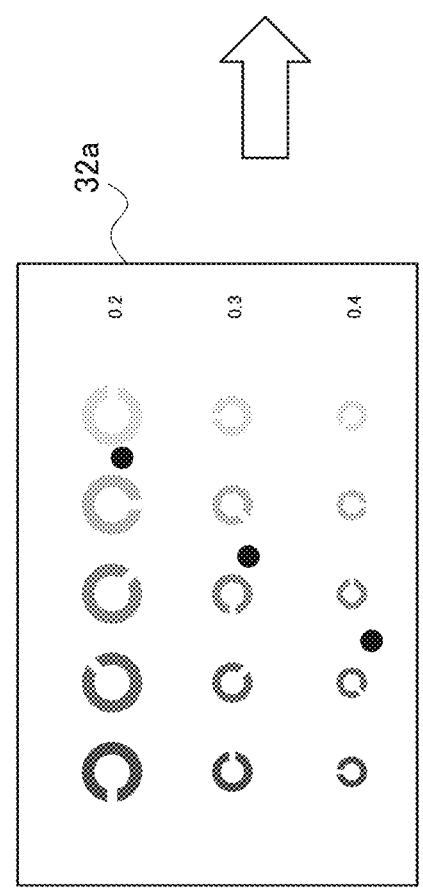
FIG.10A

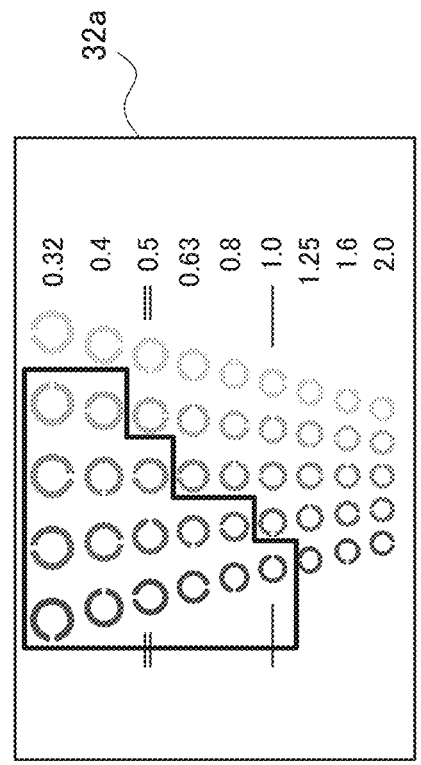
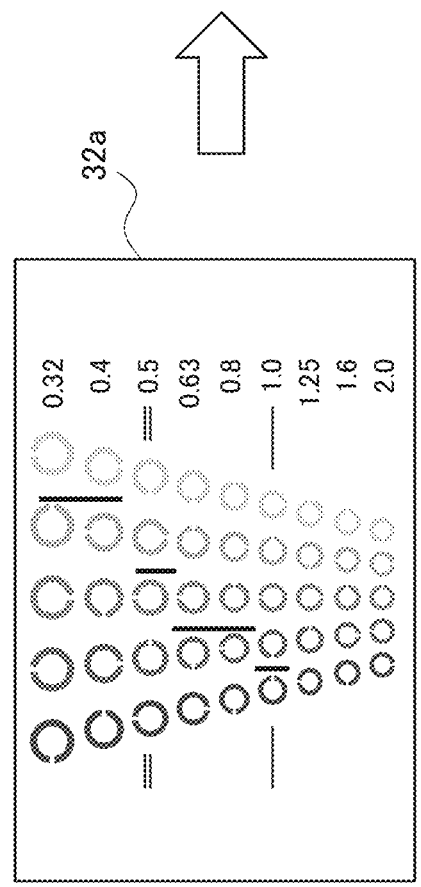
FIG.10B

CONTRAST & VISUAL ACUITY VALUE

FIG.12
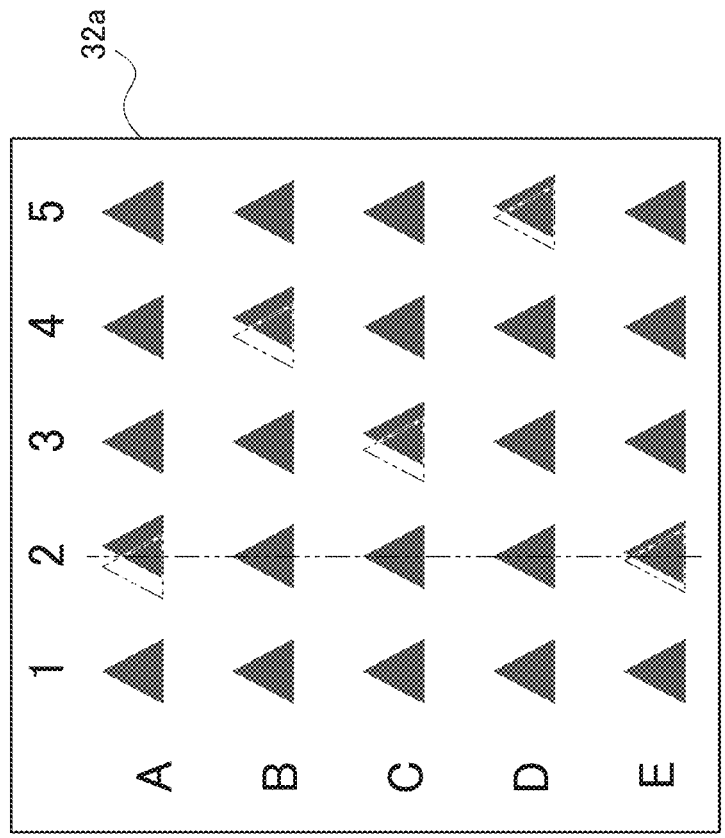
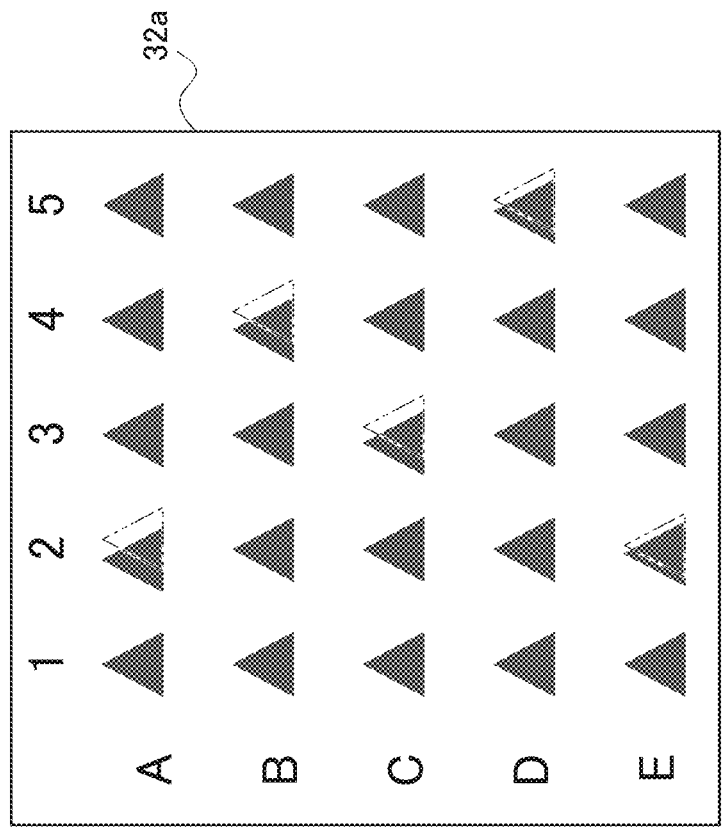

FIG.18A

```
---- Data by exam dist. ----        Test data of each test distance
         SPH    VA
  5.0m  ─────────────────────────┐  Test distance 1
  <R>   -1.25   1.0               ├  Test distance 1
  <L>   -1.00   1.0               │  Spherical power/visual acuity
  <R+L>         1.25              ┘  measured with Test distance 1

1.5m  ─────────────────────────┐  Test distance 2
  <R>   -0.50   1.0               │  Spherical power/visual acuity
  <L>   -0.25   1.0               │  measured with Test distance 2
  <R+L>         1.25              ┘

80cm  ─────────────────────────┐  Test distance 3
  <R>    0.00   1.0               │  Spherical power/visual acuity
  <L>   +0.25   1.0               │  measured with Test distance 3
  <R+L>         1.25              ┘

60cm  ─────────────────────────┐  Test distance 4
  <R>   +0.50   1.0               │  Spherical power/visual acuity
  <L>   +0.75   1.0               │  measured with Test distance 4
  <R+L>         1.25              ┘

40cm  ─────────────────────────┐  Test distance 5
  <R>   +1.25   1.0               │  Spherical power/visual acuity
  <L>   +1.50   1.0               │  measured with Test distance 5
  <R+L>         1.25              ┘
```

FIG.18B

| Data by exam dist. | 5.0m | | 1.5m | | 80cm | | 60cm | | 40cm | |
|---|---|---|---|---|---|---|---|---|---|---|
| | R | L | R | L | R | L | R | L | R | L |
| Sph | -1.25 | -1.00 | -0.50 | -0.25 | 0.00 | +0.25 | +0.50 | +0.75 | +1.25 | +1.50 |
| VA | 1.0 | 1.0 | 1.0 | 1.0 | 1.0 | 1.0 | 1.0 | 1.0 | 1.0 | 1.0 |
| | 1.25 | | 1.25 | | 1.25 | | 1.25 | | 1.25 | |

OPHTHALMOLOGIC APPARATUS AND MEASUREMENT METHOD USING THE SAME

CROSS-REFERENCE TO RELATED APPLICATION

The present application is based on and claims priority to U.S. Provisional Application No. 63/191,575 filed on May 21, 2021, the disclosure of which is hereby incorporated by reference in its entirety.

FIELD OF THE INVENTION

The present disclosure relates to an ophthalmologic apparatus and a measurement method using the ophthalmologic apparatus.

BACKGROUND

In order to treat a cataract and correct refractive power, a technique of inserting an artificial lens called an intraocular lens (IOL) into an eye by surgery is known (see, for example, JP 2020-22762A). For the cataract treatment, the crystalline lens is removed from the lens capsule and an intraocular lens is inserted into the lens capsule. In addition, various intraocular lenses have been developed, such as a phakic intraocular lens (phakic IOL) that is inserted and fixed between the cornea and the iris without removing the crystalline lens, and a phakic IOL that is inserted and fixed between the iris and the crystalline lens without removing the crystalline lens, as well as an intraocular lens that is inserted into the lens capsule.

The intraocular lens can be focused at a plurality of distances such as a far point, a near point, and a midpoint r intermediate point so that a wearer of the intraocular lens can live a daily life without any trouble. There are also intraocular lenses that can correct astigmatism. Therefore, in order to grasp whether the intraocular lenses function appropriately, it is desirable to measure the characteristics of the eye to be examined (also referred to as subject eye hereinafter) at a plurality of examination distances (i.e., distances from subject eye to visual targets) from the far-point distance to the near-point distance. In addition, in order to grasp the characteristics of the subject eyes in more detail, such as how the visual targets appear to the eyes at night, various examinations such as a contrast examination for measuring contrast sensitivity of the subject eyes by changing the contrast of each visual target, a glare examination for examining the subject eyes in a glaring state (glare) by irradiating the subject eyes with light, and the like are performed (see, for example, JP 2019-136569A). It is desirable that these examinations also measure how the visual targets appear at various examination distances.

In addition, as a method of correcting the refractive power of the subject eye, there is a therapeutic method called orthokeratology in which a dedicated contact lens is worn in the eye before sleeping and the shape of the cornea is changed during sleep to correct myopia, a LASIK treatment in which the cornea is irradiated with laser light to correct myopia, and the like. Furthermore, soft contact lenses, hard contact lenses, and the like that are generally used also include lenses having functions such as bifocal and astigmatism correction. With regard to the characteristics of the subject eye corrected by the above methods and lenses, it is desirable to perform a plurality of examinations using various visual targets at various distances.

However, in the case of measuring the characteristics of the subject eye by changing the examination distances, an examinee or subject needs to move closer to and away from a visual acuity chart on which visual targets are displayed when being measured. This takes time for the examination and the subject may be fatigued, which may affect the efficiency and accuracy of the measurement. In addition, the focal length is variously set depending on the type of the intraocular lens and the like, and the contrast sensitivity and the like may also vary. Therefore, it is desired to develop a technology capable of efficiently performing various examinations by changing the examination distances and the presentation condition of the visual targets according to the characteristics of the intraocular lens and the correction state of the subject eye.

SUMMARY

The present disclosure has been made in view of the above circumstances, and an object of the present disclosure is to provide an ophthalmologic apparatus that changes examination distances and presentation conditions of visual targets as desired and quickly and easily measures the characteristics of a subject eye at various examination distances under various presentation conditions, thereby improving measurement efficiency.

In order to achieve the above object, an ophthalmologic apparatus of the present disclosure includes a visual target projection system that is configured to present a visual target to a subject eye at a predetermined examination distance under a presentation condition according to the examination distance, and a controller that is configured to control the visual target projection system. The controller is configured to control the visual target projection system to present the visual target at a first examination distance for a far-point examination of the subject eye, a second examination distance for a near-point examination of the subject eye, and at least one third examination distance different from the first examination distance and the second examination distance.

BRIEF DESCRIPTION OF DRAWINGS

FIG. 9 is a flowchart describing an example of the operation of the ophthalmologic apparatus according to the present embodiment.

FIG. 10A is a view illustrating a display state of visual targets on a display of an ophthalmologic apparatus according to a modification, the view illustrating a state in which marks corresponding to a tap operation by a subject are superimposed on the visual targets and displayed, and a state in which a measurement result is displayed.

FIG. 10B is a view illustrating a display state of visual targets on the display of the ophthalmologic apparatus according to the modification, the view illustrating a state in which marks corresponding to a drag operation by the subject are superimposed on visual targets and displayed, and a state in which a measurement result is displayed.

FIG. 12 is a view illustrating a display example of the visual targets for the precise stereoscopic vision test on the display, the view illustrating a display example on the display for a left eye on a left side of the view, and a display example on the display for a right eye in a right side of the view.

FIG. 18A is a view illustrating an ophthalmologic apparatus according to another embodiment of the present disclosure, the view illustrating an output sample of measurement results.

FIG. 18B is a view illustrating an ophthalmologic apparatus according to another embodiment of the present disclosure, the view illustrating another output sample of the measurement results.

DETAILED DESCRIPTION

Figure 1:
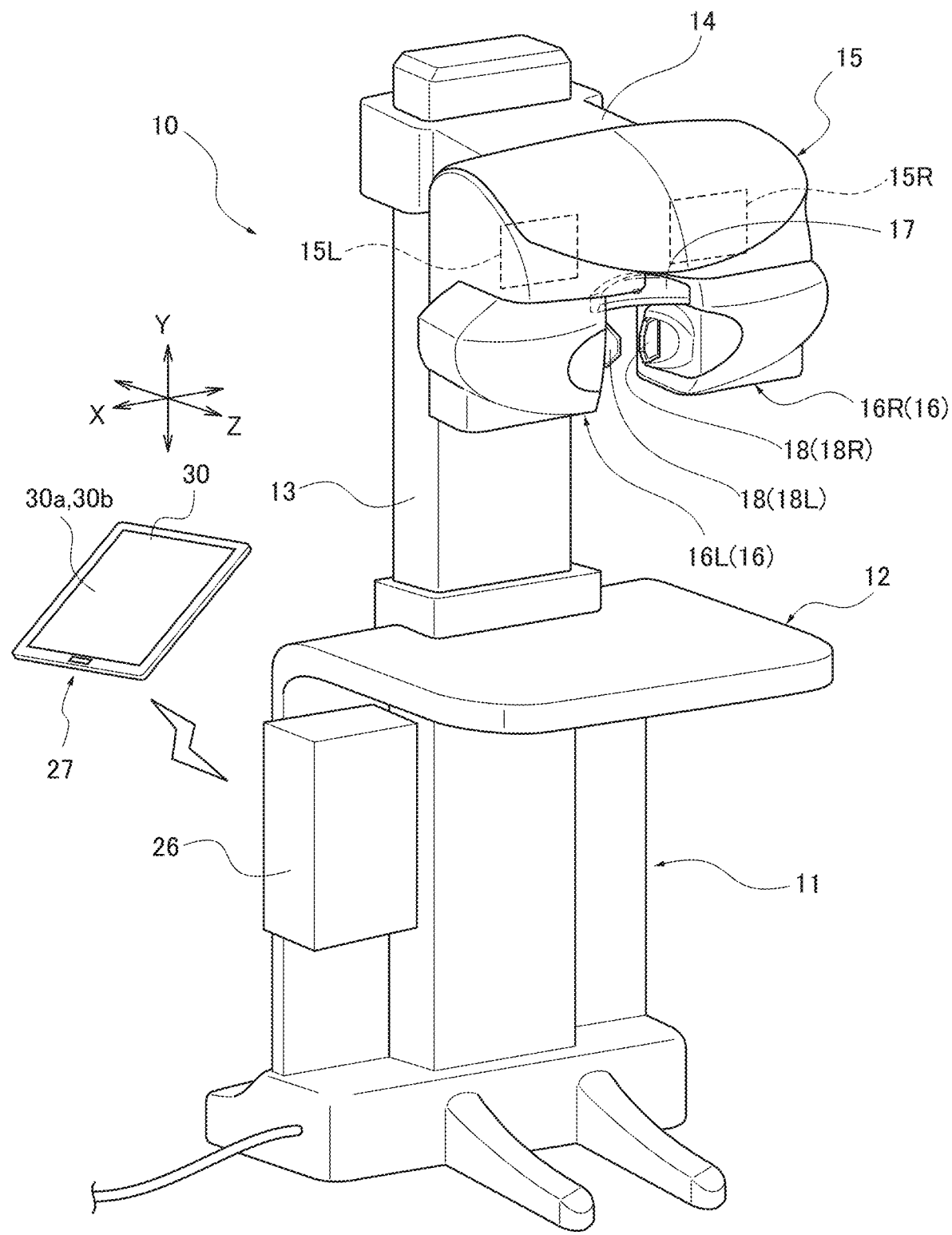
FIG. 1 is a perspective view illustrating an overall configuration of an ophthalmologic apparatus according to the present embodiment.

With respect to the use of plural and/or singular terms herein, those having skill in the art can translate from the plural to the singular and/or from the singular to the plural as is appropriate to the context and/or application. The various singular/plural permutations may be expressly set forth herein for sake of clarity.

First Embodiment

Hereinafter, an ophthalmologic apparatus according to a first embodiment will be described. First, an overall configuration of the ophthalmologic apparatus 10 according to the first embodiment will be described with reference to FIGS. 1 to 5. The ophthalmologic apparatus 10 according to the present embodiment is a binocular opening (bind-open) type ophthalmologic apparatus capable of simultaneously measuring characteristics of subject eyes in a state where the subject opens the left and right eyes (i.e., binocular condition). In the ophthalmologic apparatus according to the present embodiment, it is also possible to examine each eye one by one by shielding one of the eyes or turning off a fixation target. In addition, the ophthalmologic apparatus is not limited to the binocular opening type, and the present disclosure may also be applied to an ophthalmologic apparatus that measures characteristics of both eyes one by one.

Furthermore, the ophthalmologic apparatus 10 according to the present embodiment is configured to measure characteristics of the subject eye (eye to be examined) in a corrected state, such as the subject eye into which an intraocular lens (IOL) is inserted, at various examination distances (distances from subject eye to presentation position of visual targets) under various measurement conditions (such as examination type, procedure, visual target presentation condition, and the like). Examples of the intraocular lens include, but are not limited to, a monofocal (single-focal) intraocular lens, a bifocal intraocular lens (multifocal IOL) such as a multifocal intraocular lens or a progressive intraocular lens, an intraocular lens (premium IOL) with an astigmatism correction function, and a phakic intraocular lens (phakic IOL). In addition, the ophthalmologic apparatus 10 can also be used to measure the characteristics of the subject eye after orthokeratology treatment with a special contact lens, the subject eye after laser treatment, the subject eye with a soft contact lens or a hard contact lens, and the subject eye with glasses.

The ophthalmologic apparatus 10 according to the present embodiment is configured to perform an arbitrary subjective examination and further perform an objective examination. In the subjective examination, the ophthalmologic apparatus 10 presents visual targets or the like to the subject at a predetermined presentation position and acquires an examination result in accordance with a response of the subject to the visual targets or the like. The subjective examination includes subjective refraction measurement such as far-point examination, midpoint examination, near-point examination, contrast examination, and glare examination, visual field examination, and the like. In the objective examination, the ophthalmologic apparatus 10 irradiates the subject eyes with light and measures information (eye characteristics) on the subject eyes based on the result of detecting the return light. The objective examination includes measurement for acquiring characteristics of the subject eyes and photographing for acquiring images of the subject eyes. Furthermore, the objective examination includes objective refraction measurement (refraction measurement), corneal shape measurement (keratometry), intraocular pressure measurement, fundus photography, tomographic imaging (optical coherence tomography imaging) using optical coherence tomography (Optical Coherence Tomography: referred to as "OCT" hereinafter), measurement using OCT, and the like.

(Overall Configuration of Ophthalmologic Apparatus) As illustrated in FIG. 1, the ophthalmologic apparatus 10 according to the present embodiment includes a base 11, an optometry table 12, a support column 13, an arm 14, a drive mechanism (drive portion) 15, and a pair of measurement heads 16. The ophthalmologic apparatus 10 acquires information of the subject eyes in a state where the subject facing the optometry table 12 puts his or her forehead on a forehead rest 17 which is provided between the two measurement heads 16. An X-axis, a Y-axis, and a Z-axis are defined as shown in FIG. 1, which are used throughout the specification. Specifically, when viewed from the subject, a horizontal direction is defined as an X direction, a vertical direction (top-bottom direction) is defined as a Y direction, and a direction (depth direction of measurement heads 16) orthogonal to the X direction and the Y direction is defined as a Z direction.

The optometry table 12 is a desk for placing a display and examiner controller 27 (hereinafter, simply referred to as an "examiner controller"), a subject controller 28, which will be described later, and an object to be used for optometry. The optometry table 12 is supported by the base 11. The optometry table 12 may be supported by the base 11 such that the position (height) of the optometry table 12 in the Y direction is adjustable.

The support column 13 is supported by the base 11 to extend in the Y direction at the rear end of the optometry table 12, and the arm 14 is provided at the distal end of the support column 13. The arm 14 suspends the measurement heads 16 via the drive mechanism 15 above the optometry table 12 and extends in the Z direction from the support column 13 toward the front side. The arm 14 is movable in the Y direction with respect to the support column 13. Note that the arm 14 may be movable in the X direction and the Z direction with respect to the support column 13. The pair of measurement heads 16 suspended by the drive mechanism 15 is supported at the distal end of the arm 14.

The measurement heads 16 are provided as a pair to respectively correspond to the left and right eyes of the subject. Hereinafter, when individually described, the measurement heads 16 are referred to as a left-eye measurement head 16L and a right-eye measurement head 16R. The left-eye measurement head 16L is configured to acquire information of the left eye of the subject, and the right-eye measurement head 16R is configured to acquire information of the right eye of the subject. The left-eye measurement head 16L and the right-eye measurement head 16R are arranged to be plane-symmetrical with respect to a vertical plane located at the center between the measurement heads 16L, 16R in the X direction.

Each of the measurement heads 16 is provided with a mirror 18 which is a deflection member. Information of the corresponding subject eye is acquired by a measurement optical system 21, which will be described later, through the mirror 18.

Each of the measurement heads 16 is provided with a measurement optical system 21 that acquires information of the subject eye. Hereinafter, the measurement optical systems 21 are referred to as a right-eye measurement optical system 21R and a left-eye measurement optical system 21L when individually described. The detailed configuration of the measurement optical systems 21 will be described later.

Figure 2:
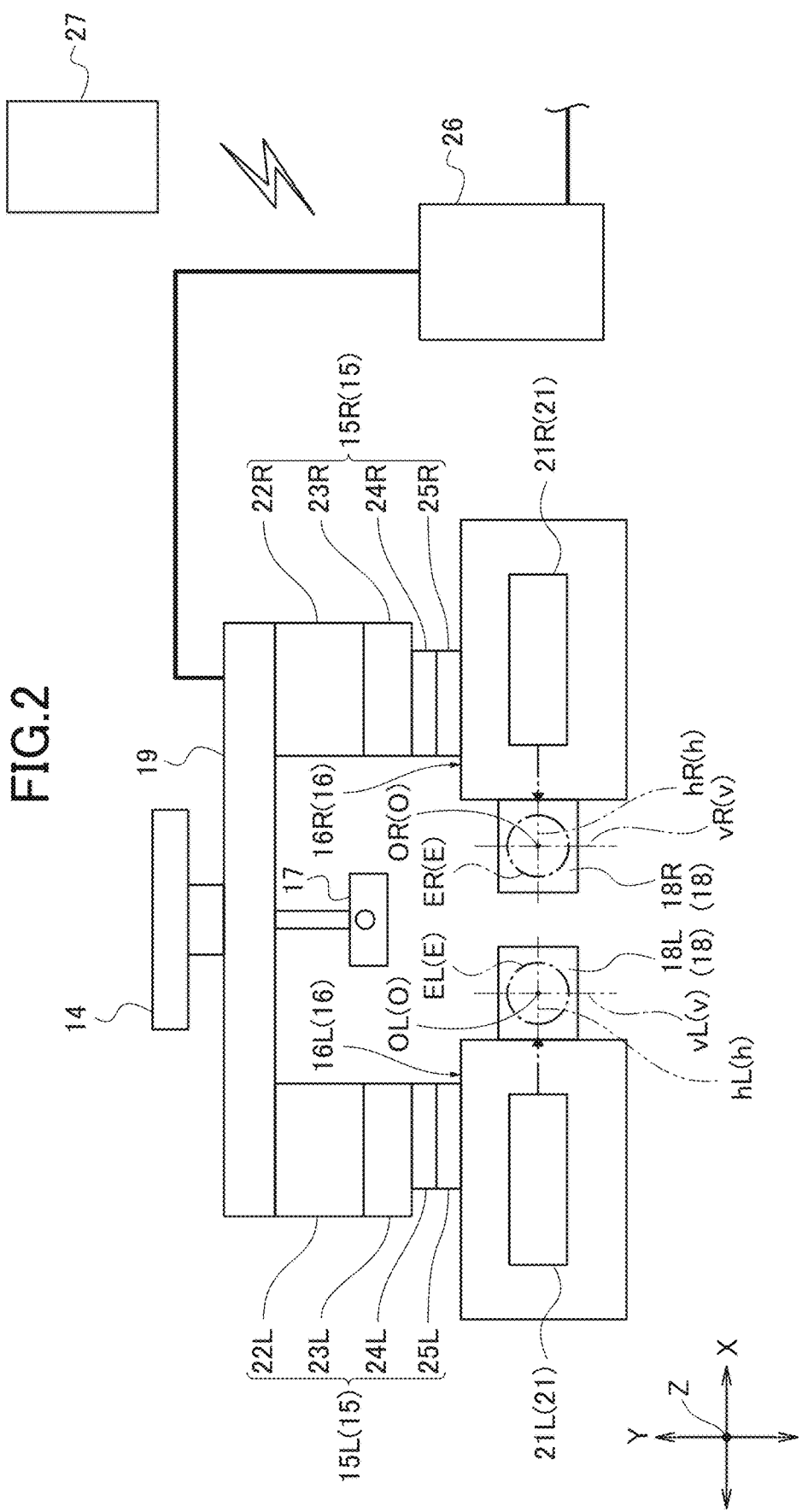
FIG. 2 is a block diagram illustrating the overall configuration of the ophthalmologic apparatus according, to the present embodiment.

The two measurement heads 16 are movably suspended by the drive mechanism 15 provided at a base 19 that is suspended from the distal end of the arm 14. In the present embodiment, as illustrated in FIG. 2, the drive mechanism 15 includes a left-eye drive mechanism 15L corresponding to the left-eye measurement head 16L and a right-eye drive mechanism 15R corresponding to the right-eye measurement head 16R. The left-eye drive mechanism 15L includes a left-eye vertical drive portion 22L, a left-eye horizontal drive portion 23L, a left-eye X-direction rotation drive portion (left-eye horizontal rotation drive portion) 24L, and a left-eye Y-direction rotation drive portion (left-eye vertical rotation drive portion) 25L. The right-eye drive mechanism 15R includes a right-eye vertical drive portion 22R, a right-eye horizontal drive portion 23R, a right-eye X-direction rotation drive portion (right-eye horizontal rotation drive portion) 24R, and a right-eye Y-direction rotation drive portion (right-eye vertical rotation drive portion) 25R.

The drive portions corresponding to the left-eye measurement head 16L and the drive portions corresponding to the right-eye measurement head 16R are plane-symmetrical with respect to the vertical plane located at the center between the left-eye and right-eye measurement heads 16L, 16R in the X direction. Hereinafter, the drive portions may be referred to as vertical drive portions 22, horizontal drive portions 23, X-direction rotation drive portions 24, and Y-direction rotation drive portions 25 unless otherwise individually described. The same applies to other components provided symmetrically on the left and right.

As illustrated in FIG. 2, in the drive mechanism 15, the vertical drive portions 22, the horizontal drive portions 23, the X-direction rotation drive portions 24, and the Y-direction rotation drive portions 25 are arranged in this order from the upper side.

The vertical drive portions 22 are fixed to the base 19 at the distal end of the arm 14 and move the horizontal drive portions 23, the X-direction rotation drive portions 24, and the Y-direction rotation drive portions 25 in the Y direction (vertical direction) with respect to the arm 14 in response to a control signal from a controller 26. The horizontal drive portions 23 are fixed to the vertical drive portions 22 and move the X-direction rotation drive portions 24 and the Y-direction rotation drive portions 25 in the X direction and the Z direction (horizontal direction) with respect to the vertical drive portions 22 in response to the control signal from the controller 26.

Each of the vertical drive portions 22 and the horizontal drive portions 23 includes an actuator that may be a pulse motor or the like to generate a driving force and a transmission mechanism that is a combination of gears, a rack, and a pinion, or the like to transmit the driving force. Each of the horizontal drive portions 23 is easily configured and easily controls movement in the horizontal direction, for example, by individually providing a combination of an actuator and a transmission mechanism in each of the X direction and the Z direction.

The X-direction rotation drive portions 24 are connected to the horizontal drive portions 23. In response to the control signal from the controller 26, the X-direction rotation drive portions 24 rotate the measurement heads 16 and the Y-direction rotation drive portions 25 corresponding to the horizontal drive portions 23 in the X direction (horizontal direction) about a pair of vertical eyeball rotation axes v (rotation axes). The vertical eyeball rotation axes v (also denoted as vL and vR as shown in FIG. 2 with alternate lone and short dash lines through left subject eye EL and right subject eye ER) extend in the vertical direction (i.e., Y direction) through the eyeball rotation points O (left eyeball rotation point OL and right eyeball rotation point OR in FIG. 2) of the corresponding subject eyes E.

The Y-direction rotation drive portions 25 are connected to the X-direction rotation drive portions 24. The measurement heads 16 are suspended on the Y-direction rotation drive portions 25. In response to the control signal from the controller 26, the Y-direction rotation drive portions 25 rotate the measurement heads 16 corresponding to the X-direction rotation drive portions 24 in the Y direction (vertical direction, top-bottom direction) about a pair of horizontal eyeball rotation axes h (rotation axes). The horizontal eyeball rotation axes h (also denoted as hL and hR as shown in FIG. 2 with two-dot chain lines through left subject eye EL and right subject eye ER) extend in the horizontal direction (i.e., X direction) through the eyeball rotation points O (left eyeball rotation point OL and right eyeball rotation point OR in FIG. 2) of the corresponding subject eyes E.

The X-direction rotation drive portions 24 and the Y-direction rotation drive portions 25 may be configured such that, for example, the transmission mechanisms that have received the driving forces from the actuators move along arc-shaped guide grooves. By matching the respective center positions of the guide grooves with the pair of horizontal eyeball rotation axes h (hL, hR) and the pair of vertical eyeball rotation axes v (vL, vR), the X-direction rotation drive portions 24 and the Y-direction rotation drive portions 25 rotate the measurement heads 16 about the pair of horizontal eyeball rotation axes h (hL, hR) and the pair of vertical eyeball rotation axes v (vL, vR) of the subject eyes E.

The X-direction rotation drive portions 24 may be configured to support the Y-direction rotation drive portions 25 and the measurement heads 16 so as to be rotatable about the rotation axes thereof, and to rotate the measurement heads 16 while changing positions where the measurement heads 16 are supported in cooperation with the horizontal drive portions 23. In addition, the Y-direction rotation drive portions 25 may be configured to rotatably support the measurement heads 16 about the rotation axes thereof, and to rotate the measurement heads 16 while changing positions where the measurement heads 16 are supported in cooperation with the vertical drive portions 22.

With the above configuration, the drive mechanism 15 can move the measurement heads 16 individually or in conjunction in the X direction, the Y direction, and the Z direction, and can rotate the measurement heads 16 about the vertical eyeball rotation axes v and the horizontal eyeball rotation axes h of the subject eyes E in the X direction and the Y direction. In the ophthalmologic apparatus 10 according to the present embodiment, the drive portions 22 to 25 of the drive mechanism 15 are driven to move and rotate the measurement heads 16 in response to the control signal from the controller 26. Furthermore, an examiner or the like may manually drive each of the drive portions 22 to 25 to move and rotate each of the measurement heads 16.

In addition, the left-eye X-direction rotation drive portion 24L and the right-eye X-direction rotation drive portion 24R can cause the subject eyes E to diverge (divergence movement) or converge (convergence movement) by rotating the left-eye measurement head 16L and the right-eye measurement head 16R in the X direction (left-right direction). In addition, the left-eye Y-direction rotation drive portion 25L and the right-eye Y-direction rotation drive portion 25R can direct the lines of sight of the subject eyes E downward or return the lines to the original positions by rotating the left-eye measurement head 16L and the right-eye measurement head 16R in the Y direction (vertical direction), respectively. Thereby, the ophthalmologic apparatus 10 can conduct the examinations of the divergence movement and the convergence movement, and conduct examinations at various examination distances from a far-point examination at a far-point distance to a near-point examination at a near-point distance with the binocular vision to measure various characteristics of both subject eyes E.

Figure 3A:
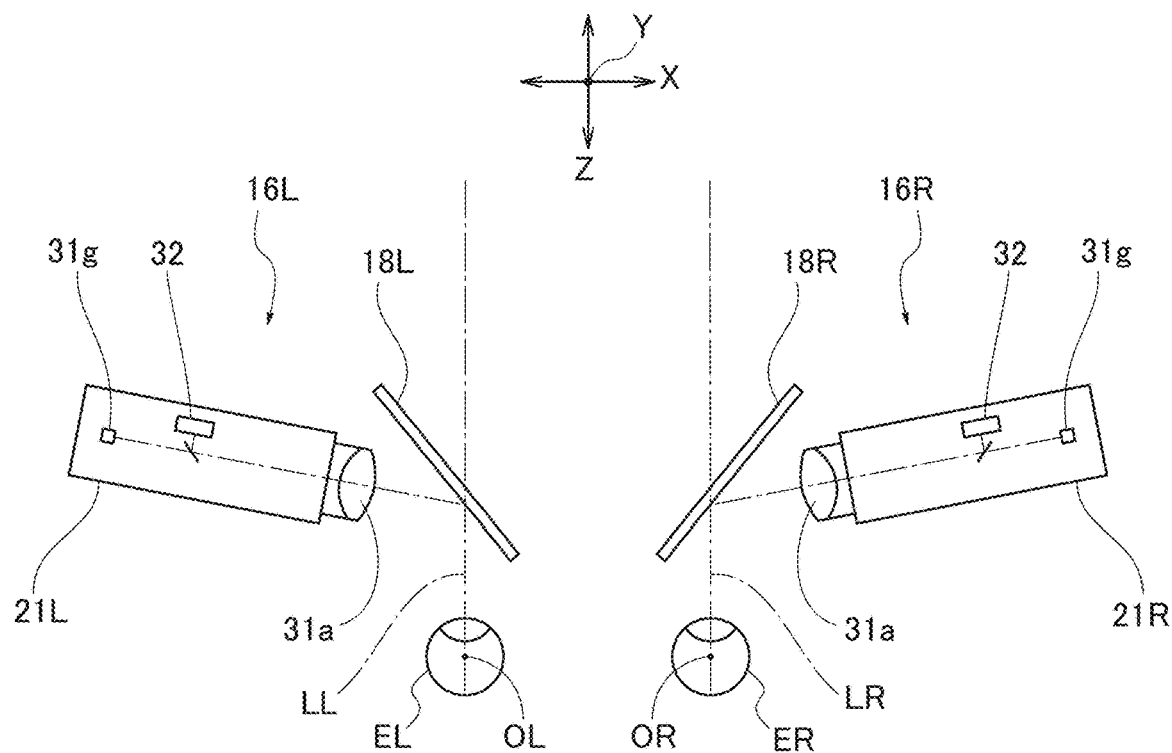
FIG. 3A is a view illustrating a relationship between the orientation of measurement heads of the ophthalmologic apparatus according to the present embodiment and visual axes, the view illustrating the orientation of the measurement heads when an infinite distance is visually recognized with binocular vision.
Figure 3B:
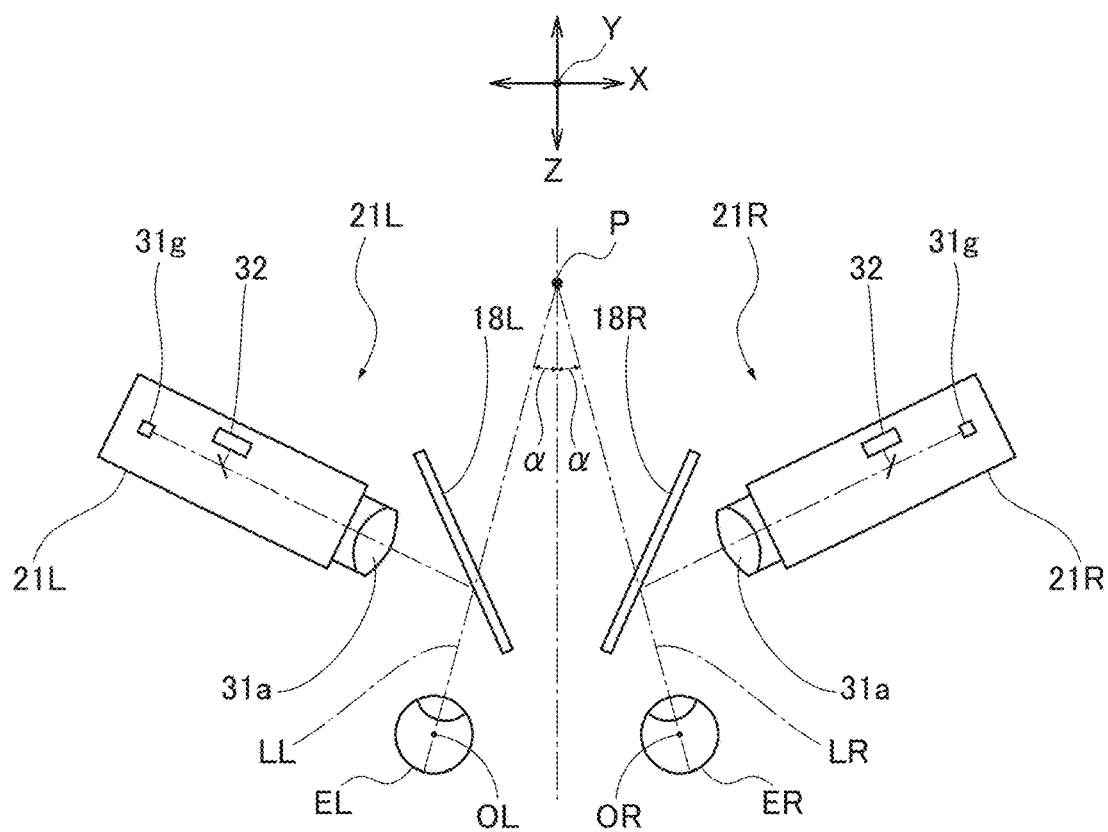
FIG. 3B is a view illustrating a relationship between the orientation of the measurement heads of the ophthalmologic apparatus according to the present embodiment and the visual axes, the view illustrating the orientation of the measurement heads when a predetermined distance is visually recognized with binocular vision.

FIG. 3A illustrates the rotational orientations of the left-eye and right-eye measurement heads 16L, 16R which are adjusted such that the optical axes LL, LR from the left and right subject eyes EL, ER to left and right mirrors 18L, 18R are parallel to each other. In the state illustrated in FIG. 3A, when visual targets (fixation images) or the like are presented to the left and right subject eyes EL, ER by a visual target projection system 32 of each of the left-eye and right-eye measurement heads 16L, 16R, visual axes of the subject can be set to be the same as or similar to visual axes in a state in which the subject looks at infinity with binocular vision. FIG. 3B illustrates the rotational orientations of the left-eye and right-eye measurement heads 16L, 16R which are adjusted such that the respective optical axes LL, LR extend from the left and right subject eyes EL, ER to a predetermined position P through the left and right mirrors 18L, 18R. In the state illustrated in FIG. 3B, when the visual target projection systems 32 of the left-eye and right-eye measurement heads 16L, 16R present the visual targets (fixation images) or the like to the left and right subject eyes EL, ER of the subject, the visual axes of the subject can be set to be the same as or similar to visual axes in a state in which the subject looks at the predetermined position P with the binocular vision. As described above, the ophthalmologic apparatus 10 can change the visual axes of the left and right subject eyes EL, ER so as to cause the eyes to converge or diverge by simultaneously changing the rotational orientations of the left-eye and right-eye measurement heads 16L, 16R symmetrically, and can direct the visual axes to the presentation position (apparent presentation position separated from subject eyes E by a predetermined examination distance, for example, position P) of the visual targets.

The ophthalmologic apparatus 10 can change the position P at which the visual targets are presented by changing rotational angles α illustrated in FIG. 3B. As illustrated in FIG. 3A, the rotational angle α is an angle based on each of the visual axes (in a state of being parallel to each other) of the subject eyes E in a state in which the subject looks at infinity. When the subject looks at infinity, the rotational angle α is 0°. In addition, the ophthalmologic apparatus 10 can provide the parallax to the visual targets presented to the left and right subject eyes E in response to the change in the rotational angles α. That is, the ophthalmologic apparatus 10 changes the rotational angles α to change the position P at which the visual targets are presented, and changes the parallax provided to the visual targets according to the change of the rotational angles α. As a result, the ophthalmologic apparatus 10 can stereoscopically present the visual targets to the subject in a state corresponding to the position P.

As illustrated in FIGS. 1 and 2, the controller 26 is disposed on the base 11. The controller 26 is configured to comprehensively control the portions or components of the ophthalmologic apparatus 10. In addition, the ophthalmologic apparatus 10 includes an examiner controller 27 to be used by the examiner to operate the ophthalmologic apparatus 10 and a subject controller 28 to be used by the subject to respond at the time of acquisition of various types of eye information of the subject eyes.

The examiner controller 27 is an information processing device that is, for example, a tablet terminal, a smartphone, or the like and is capable of performing short-range communication with the controller 26. Note that the examiner controller 27 is not limited to the tablet terminal and the like, and e examiner controller 27 may be a laptop personal computer, a desktop personal computer, or the like, or may be a controller dedicated to the ophthalmologic apparatus 10.

In the ophthalmologic apparatus 10 according to the present embodiment, the examiner controller 27 is portable. The examiner controller 27 may be placed on the optometry table 12 when operated or may be held by the examiner in hand when operated.

The subject controller 28 includes a subject input portion 28a such as a keyboard, a mouse, a joystick, a touchpad, a touchscreen, or a touch panel. The subject controller 28 is connected to the controller 26 via a wired or wireless communication path and sends an input signal corresponding to an operation received by the subject input portion 28a to the controller 26. It can be said that subject controller 28 itself is one of the subject input portions.

(Measurement Optical Systems) Each of the left-eye measurement optical system 21L and the right-eye measurement optical system 21R includes a visual acuity examination device that performs a visual acuity examination while changing visual targets to be presented, a phoropter that acquires appropriately corrected refractive power of the subject eyes while changing and arranging correction lenses, a refractometer and a wavefront sensor that measure refractive power, a fundus camera that captures an image of the fundus, a tomographic imaging device that captures a tomographic image of the retina, a spectral microscope that captures a corneal endothelial image, a keratometer that measures a corneal shape, a tonometer that measures intraocular pressure, and the like. The above devices or components are included separately or multiple combinations thereof.

Figure 5:
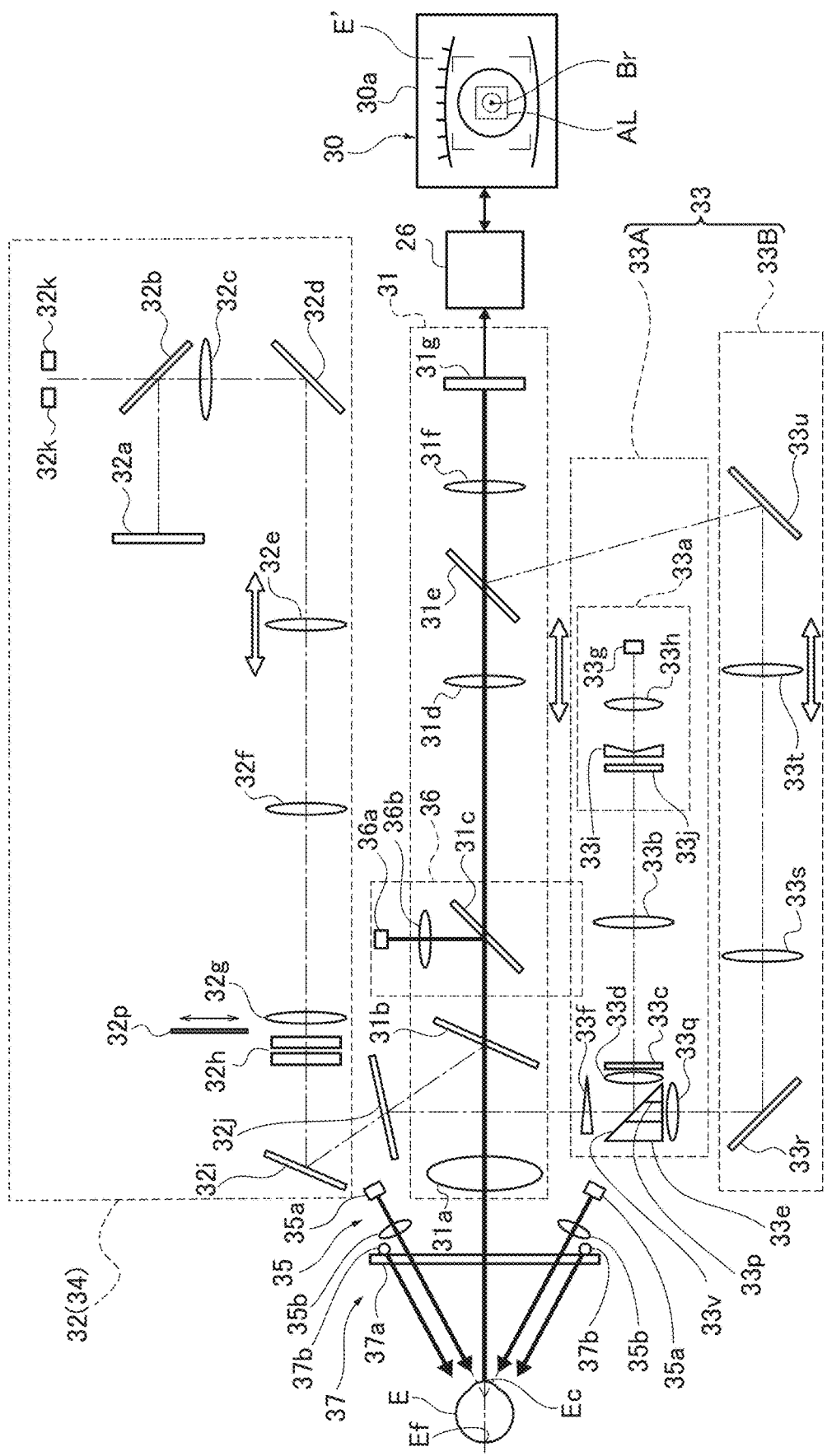
FIG. 5 is a view illustrating a detailed configuration of a right-eye measurement optical system of the ophthalmologic apparatus according to the present embodiment.

FIG. 5 is a view illustrating the detailed configuration of the right-eye measurement optical system 21R of the ophthalmologic apparatus according to the present embodiment. In FIG. 5, the mirror 18R is not shown. The right-eye measurement optical system 21R will be described while the description of the left-eye measurement optical system 21L will be omitted since the configuration of the left-eye measurement optical system 21L is the same as that of the right-eye measurement optical system 21R.

As illustrated in FIG. 5, the right-eye measurement optical system 21R includes an observation system 31, the visual target projection system 32, a subjective examination system 34, a first alignment system 35, a second alignment system 36, an eye refractive power measurement system 33, and a keratometry (KERATO) system 37. The eye refractive power measurement system 33 and the KERATO system 37 are examples of an objective measurement optical system.

The observation system 31 observes the anterior segment of the subject eye E. The visual target projection system 32 presents visual targets to the subject eye E. The eye refractive power measurement system 33 measures the refractive power of the eye. The subjective examination system 34 presents visual targets to the subject eye E and shares an optical element constituting the optical system with the visual target projection system 32. In the present embodiment, the eye refractive power measurement system 33 has a function of projecting a predetermined measurement pattern on the fundus Ef of the subject eye E and a function of detecting an image of the measurement pattern projected on the fundus Ef.

The first alignment system 35 and the second alignment system 36 perform alignment (positioning) of the optical system with respect to the subject eye E. The first alignment system 35 performs alignment in the direction (front-back direction, Z direction) along the optical axis of the observation system 31. The second alignment system 36 performs alignment in the directions (vertical and horizontal directions; Y and X directions) orthogonal to the optical axis.

The observation system 31 includes an objective lens 31a, a first dichroic filter 31b, a first half mirror 31c, a first relay lens 31d, a second dichroic filter 31e, an imaging lens 31f, and an imaging element (CCD) 31g as an image acquisition portion.

The observation system 31 forms an image of a light flux reflected by the subject eye E (anterior segment) on the imaging element 31g by the imaging lens 31f via the objective lens 31a. As a result, on the imaging element 31g, a keratometry (KERATO) ring light flux, a light flux of a first alignment light source 35a, and a light flux (bright spot image Br) of a second alignment light source 36a, which are described later, are projected to form an anterior segment image E'. The imaging element 31g of the observation system 31 captures the anterior segment image E'. The controller 26 displays the anterior segment image E' and the like based on an image signal output from the imaging element 31g on a display surface 30a of the display 30 of the examiner controller 27.

The KERATO system 37 is provided in front of the objective lens 31a. The KERATO system 37 has a keratometry (KERATO) plate 37a and a KERATO ring light source 37b. The KERATO plate 37a has a plate shape provided with a slit concentric with respect to the optical axis of the observation system 31. The KERATO plate 37a is provided in the vicinity of the objective lens 31a. The KERATO ring light source 37b is provided in accordance with the slit of the KERATO plate 37a.

In the KERATO system 37, the light flux from the KERATO ring light source 37b that has been turned on passes through the slit of the KERATO plate 37a, so that the KERATO ring light flux (ring-shaped visual target for corneal curvature measurement) for measuring the corneal shape is projected to the subject eye E (cornea Ec). The KERATO ring light flux is reflected by the cornea Ec of the subject eye E to form an image on the imaging element 31g by the observation system 31. As a result, the imaging element 31g detects (receives) the image of the ring-shaped KERATO ring light flux, and the controller 26 displays the image of the measurement pattern on the display surface 30a of the display 30, and measures the corneal shape (curvature radius) by a known method based on the image signal from the image aging element 31g).

Note that, the present embodiment illustrates, as a corneal shape measurement system, the example (KERATO system 37) using the KERATO plate 37a that has about one to three ring slits and is used to perform curvature measurement near the center of the cornea. However, the configuration of the corneal shape measurement system is not limited to the configuration of the present embodiment. As long as the corneal shape measurement system measures the corneal shape, a Placido disk or plate having multiple rings and capable of measuring the shape of the entire corneal surface may be used, or other configurations may be used.

The first alignment system 35 is provided behind the KERATO system 37 (KERATO plate 37a). The first alignment system 35 includes a pair of the first alignment light source 35a and a first projection lens 35b. The light flux from the first alignment light source 35a is converted into a parallel light flux by the first projection lens 35b, and the parallel light flux is projected to the cornea Ec of the subject eye E through an alignment hole provided in the KERATO plate 37a.

The controller 26 or the examiner performs alignment in the direction (front-back direction) along the optical axis of the observation system 31 by moving the measurement heads 16 in the front-back direction based on the bright spot (bright spot image Br) projected to the corneas Ec. This alignment in the front-back direction is performed by the controller 26 or the examiner adjusting the position of the measurement heads 16 such that the ratio of the interval between two spot images by the first alignment light source 35a on the imaging element 31g and the diameter of the KERATO ring image is within a predetermined range.

In the present embodiment, the optical axis of the measurement optical system 21 is refracted by the mirror 18, and substantially coincident with the Z-axis at the position of a mirror image formed on the mirror 18 of the measurement optical system 21. Therefore, alignment in the optical axis direction of the measurement optical system 21 corresponds to alignment in the Z direction.

Here, the controller 26 may obtain a misalignment amount from the ratio and display the misalignment amount on the display surface 30a. Note that the alignment in the front-back direction may be performed by adjusting the position of the measurement head 16R such that the bright spot image Br by the second alignment light source 36a, which will be described later, is in focus.

In addition, the observation system 31 is provided with the second alignment system (parallel optical system) 36. The second alignment system 36 includes the second alignment light source 36a and a second projection lens 36b and shares the first half mirror 31c, the first dichroic filter 31b, and the objective lens 31a with the observation system 31.

The second alignment system 36 projects the light flux from the second alignment light source (point light source) 36a to the cornea Ec of the subject eye E as a parallel light flux through the objective lens 31a. The parallel light flux projected from the second alignment system 36 to the cornea Ec of the subject eye E forms a bright spot of alignment light at a substantially intermediate position between the corneal vertex and the center of curvature of the cornea. The controller 26 or the examiner performs alignment in the directions (top-bottom and left-right directions) orthogonal to the optical axis of the observation system 31 by moving the measurement head 16 in the front-back direction based on the image (bright spot image Br) of the bright spot projected to the cornea Ec.

At this time, the controller 26 displays, on the display surface 30a, an alignment mark AL serving as a guide for the alignment, as well as the anterior segment image E' on which the bright spot image Br is formed. The controller 26 may be configured to perform control to start measurement when the alignment is completed.

The second alignment light source 36a is a light emitting diode that emits infrared light (for example, 940 nm) to prevent the subject from visually recognizing the second alignment light source 36a during the alignment operation by the second alignment system 36.

The visual target projection system 32 (subjective examination system 34) is an optical system that projects the visual target and presents the visual target to the eye fundus Ef to cause the subject eye E to fixate the visual target and fog the subject eye E. The visual target projection system 32 includes a display 32a, a second half mirror 32b, a second relay lens 32c, a first reflection mirror 32d, a first focusing lens 32e, a third relay lens 32f, a first field lens 32g, a variable cross cylinder lens (VCC) 32h, a second reflection mirror 32i, and a third dichroic filter 32j, and shares the first dichroic filter 31b and the objective lens 31a with the observation system 31. In addition, the subjective examination system 34 includes at least two glare light sources 32k that irradiate the subject eye E with glare light at a position surrounding the optical axis on an optical path different from an optical path to the display 32a and the like.

The display 32a presents a fixation target or a point visual target as a visual target for fixing the line of sight of the subject eye E at the time of the objective examination or the like and presents a subjective examination visual target for subjectively examining the characteristics (visual acuity value, correction power (far-point power, near-point power), and the like) of the subject eye E. The display 32a uses electroluminescence (EL) or a liquid crystal display (LCD) and displays an arbitrary image under the control of the controller 26. The display 32a is provided at a position conjugate with the eye fundus Ef of the subject eye E on the optical path of the visual target projection system 32 (subjective examination system 34).

The first focusing lens 32e is driven forward and backward along the optical axis by a drive motor (not shown). By moving the first focusing lens 32e toward the subject eye E, the refractive power can be reduced. By moving the first focusing lens 32e away from the subject eye E, the refractive power can be increased. Therefore, the visual target projection system 32 can change the examination distance from the presentation position of the visual target displayed on the display 32a to the subject eye E by moving the first focusing lens 32e forward and backward. That is, the visual target projection system 32 can change the presentation position of the visual target image and can cause the subject eye E to fixate the visual target image and fog the subject eye E.

In addition, the visual target projection system 32 (subjective examination system 34) includes a pinhole plate 32p at a position (between first field lens 32g and VCC 32h in present embodiment) substantially conjugate with the pupil of the subject eye E on the optical path. The pinhole plate 32p is formed by providing a through-hole in a plate member. The pinhole plate 32p is inserted into the optical path of the visual target projection system 32 (subjective examination system 34) and removed from the optical path under the control of the controller 26. The insertion of the pinhole plate 32p into the optical path places the through-hole on the optical axis. The pinhole plate 32p is inserted into the optical path at the time of the subjective examination, thereby making it possible to perform a pinhole test for determining whether or not the subject eye E can be corrected with glasses. Note that the pinhole plate 32p is not limited to the configuration of the present embodiment and may be provided at a position substantially conjugate with the pupil of the subject eye E on the optical path.

The visual target displayed on the display 32a in the subjective examination or the like is not particularly limited as long as it is used for optometry. For example, the visual target includes a Landolt ring, a Snellen visual target, an E-chart, and the like. Furthermore, various visual targets may be used such as a visual target including a character or a letter such as hiragana or katakana, which are Japanese letters, a drawing such as an animal and a finger, or a visual target including a specific figure for binocular vision function optometry, such as a cross visual target, a landscape picture, a landscape photograph, and the like. In addition, the visual target may be a still image or a video image. In the present embodiment, since the visual target projection system 32 includes the display 32a including an LCD or the like, it is possible to display a visual target having a desired shape, form, and contrast at a predetermined examination distance, and it is possible to perform multifaceted and detailed optometry. In addition, the ophthalmologic apparatus 10 includes the two displays 32a corresponding to the left and right subject eyes E respectively, and accordingly, it is possible to display the visual targets providing the parallax corresponding to the predetermined examination distance (presentation position), and it is possible to easily and precisely perform the stereoscopic vision examination in the natural direction of the visual axis.

The eye refractive power measurement system 33 includes a ring-shaped light flux projection system 33A and a ring-shaped light flux reception system 33B. The ring-shaped light flux projection system 33A projects a ring-shaped measurement pattern onto the eye fundus Ef of the subject eye E. The ring-shaped light flux reception system 33B detects or receives the reflected light of the ring-shaped measurement pattern from the eye fundus Ef.

The ring-shaped light flux projection system 33A includes a refraction (refractometry) light source portion 33a, a fourth relay lens 33b, a pupil ring diaphragm 33c, a second field lens 33d, an aperture prism 33e, and a rotary prism 33f. The ring-shaped light flux projection system 33A shares the third dichroic filter 32j with the visual target projection system 32 and shares the first dichroic filter 31b and the objective lens 31a with the observation system 31. The refraction light source portion 33a includes, for example, a refraction measurement light source 33g for refraction measurement using an LED, a collimator lens 33h, a conical prism 33i, and a ring pattern forming plate 33j, which are integrally movable on the optical axis of the eye refractive power measurement system 33 under the control of the controller 26.

The ring-shaped light flux reception system 33B includes a hole portion 33p of the aperture prism 33e, a third field lens 33q, a third reflection mirror 33r, a fifth relay lens 33s, a second focusing lens 33t, and a fourth reflection mirror 33u. The ring-shaped light flux reception system 33B shares the objective lens 31a, the first dichroic filter 31b, the second dichroic filter 31e, the imaging lens 31f, and the imaging element 31g with the observation system 31, shares the third dichroic filter 32j with the visual target projection system 32 and shares the rotary prism 33f and the aperture prism 33e with the ring-shaped light flux projection system 33A.

Next, the operation of the eye refractive power measurement system 33 at the time of the eye refractive power measurement will be described. The controller 26 turns on the refraction measurement light source 33g and moves the refraction light source portion 33a of the ring-shaped light flux projection system 33A and the second focusing lens 33t of the ring-shaped light flux reception system 33B in the optical axis direction. In the ring-shaped light flux projection system 33A, the refraction light source portion 33a emits a ring-shaped measurement pattern. The measurement pattern travels to the aperture prism 33e through the fourth relay lens 33b, the pupil ring diaphragm 33c, and the second field lens 33d. Then, the measurement pattern is reflected by a reflection surface 33v of the aperture prism 33e and guided to the third dichroic filter 32j through the rotary prism 33f. The ring-shaped light flux projection system 33A guides the measurement pattern to the objective lens 31a through the third dichroic filter 32j and the first dichroic filter 31b, thereby projecting the ring-shaped measurement pattern onto the eye fundus Ef of the subject eye E.

In the ring-shaped light flux reception system 33B, the ring-shaped measurement pattern formed in the eye fundus Ef is condensed by the objective lens 31a and travels to the hole portion 33p of the aperture prism 33e through the first dichroic filter 31b, the third dichroic filter 32j, and the rotary prism 33f. The ring-shaped light flux reception system 33B forms an image of the measurement pattern on the imaging element 31g after the measurement pattern passes through the third field lens 33q, the third reflection mirror 33r, the fifth relay lens 33s, the second focusing lens 33t, the fourth reflection mirror 33u, the second dichroic filter 31e, and the imaging lens 31f. As a result, the imaging element 31g detects the image of the ring-shaped measurement pattern, and the controller 26 displays the image of the measurement pattern on the display surface 30a and measures the cylindrical power (astigmatism degree), the axis angle (cylinder axis), and the spherical power (or degree) as the eye refractive power by a known method based on an image signal from the image (the imaging element 31g).

In addition, at the time of measuring the eye refractive power, the controller 26 controls the display 32a of the visual target projection system 32 to display a fixed visual target. The light flux from the display 32a is projected to the fundus Ef of the subject eye E through the second half mirror 32b, the second relay lens 32c, the first reflection mirror 32d, the first focusing lens 32e, the third relay lens 32f, the first field lens 32g, the VCC 32h, the second reflection mirror 32i, the third dichroic filter 32j, the first dichroic filter 31b, and the objective lens 31a. The examiner or the controller 26 performs alignment in a state where the subject visually fixates the presented fixed visual target, moves the first focusing lens 32e to the far point of the subject eye E based on the result of temporary measurement of the eye refractive power (refraction), and then moves the first focusing lens 32e to a position that is out of focus to bring the eye into a foggy state. As a result, the subject eye E becomes an adjustment resting state (crystalline lens is in non-adjustment state), and the eye refractive power is measured in the adjustment resting state.

Note that the configurations of the eye refractive power measurement system 33, the first alignment system 35, the second alignment system 36, the KERATO system 37, and the like, the principles of the measurement of the eye refractive power (refraction), the principles of the subjective examination, and the principles of the measurement of the corneal shape (cornea), and the like are known, and thus, detailed descriptions thereof are omitted.

Figure 4:
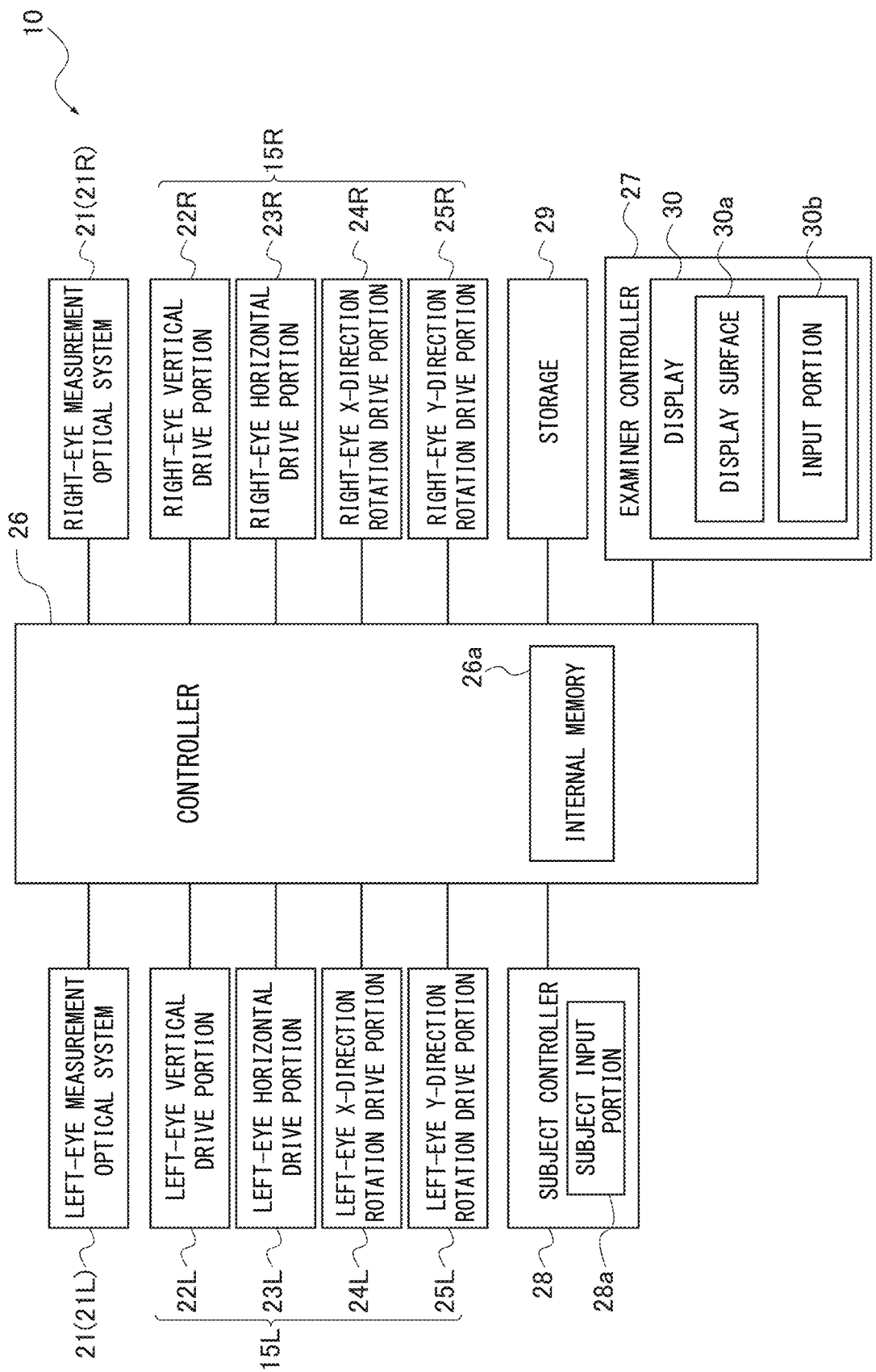
FIG. 4 is a block diagram illustrating a configuration of a control system of the ophthalmologic apparatus according to the present embodiment.

(Control System of Ophthalmologic Apparatus) The functional configuration of the controller 26 of the ophthalmologic apparatus 10 according to the present embodiment will be described with reference to FIG. 4. As illustrated in FIG. 4, the controller 26 is connected to the examiner controller 27, the subject controller 28, and a storage 29 as well as the left-eye measurement optical system 21L, the right-eye measurement optical system 21R, the left-eye vertical drive portion 22L, the left-eye horizontal drive portion 23L, the left-eye X-direction rotation drive portion 24L, the left-eye Y-direction rotation drive portion 25L of the left-eye drive mechanism 15L, and the right-eye vertical drive portion 22R, the right-eye horizontal drive portion 23R, the right-eye X-direction rotation drive portion 24R, and the right-eye Y-direction rotation drive portion 25R of the right-eye drive mechanism 15R.

The examiner controller 27 includes the display 30 which is a touch panel display. The display 30 includes the display surface 30a on which an image or the like is displayed, and a touch panel type input portion (examiner input portion) 30b superimposed and arranged on the display surface 30a. It can be said that the examiner controller 27 itself is one of the examiner input portions. The examiner controller 27 displays a predetermined image such as the anterior segment images E' acquired by the imaging elements 31g on the display surface 30a in response to the display control signal transmitted from the controller 26. In addition, the examiner controller 27 is capable of short-range communication with the controller 26 by using a communication technique such as short-range wireless communication and sends an input signal corresponding to an operation received by the input portion 30b to the controller 26.

The controller 26 includes an internal memory 26a. The controller 26 is capable of short-range wireless communication with the examiner controller 27 and the subject controller 28 via a communication portion. In addition, the controller 26 loads programs stored in the storage 29 or the internal memory 26a to, for example, a RAM, thereby comprehensively controlling the operation of the ophthalmologic apparatus 10 according to the operation performed on the examiner controller 27 or the subject controller 28 as appropriate. In the present embodiment, the internal memory 26a includes a RAM or the like, and the storage 29 includes a ROM, an EEPROM, or the like.

The controller 26 functions as a measurement condition setting portion, and controls the measurement optical systems 21 according to the type of examination to measure the eye characteristics. The measurement condition includes, for example, the type of examination in the objective examination and subjective examination, which are described above, the presentation condition of the visual target used at the time of the examination, and the like. Furthermore, the controller 26 functions as a visual target control portion, sets the presentation condition of the visual targets to be presented to the subject to a predetermined condition, and controls the visual target projection systems 32 based on the presentation condition to display the visual targets on the displays 32a. At this time, the controller 26 controls the display 30 to display the same visual targets displayed on the displays 32a on the display surface 30a of the display 30 so that the examiner also recognizes the visual targets displayed on the displays 32a. The presentation conditions include, for example, a visual acuity value, an examination distance, the type of examinations, the type of visual targets, the enlargement magnification of the visual targets, and a display mode of the visual targets. These presentation conditions can be input by the examiner from the input portion 30b of the examiner controller 27 at the time of examination, but in the present embodiment, an examination mode is set according to the type of the intraocular lens and the like, and an examination mode list in which an appropriate presentation condition is set in advance for each examination mode is stored in the storage 29 in an updatable manner. Then, when the examiner selects an examination mode from the input portion 30b, the controller 26 that has received an instruction signal in accordance with this selection acquires a presentation condition corresponding to the selected examination mode from the storage 29.

In a case where the examination mode is set for each intraocular lens, examples of the examination mode include "a single-focal IOL examination mode", "a multi-focal IOL examination mode", and "aphakic IOL examination mode". It is desirable that these setting values can be arbitrarily set or changed, for example, in an ophthalmic clinic, an eyeglass shop, a contact lens shop, a health examination center, and other facilities. Thereby, for example, it is possible to set information according to the product to be used in each facility, the correction method, the type of examination to be performed in each facility, and the like, and more appropriate examination can be performed.

The visual acuity value is used for the examinations, and a predetermined visual acuity value (for example, "1.0" or the like) is set when one visual target is presented, and a plurality of predetermined visual acuity values or ranges (for example, "0.4 to 1.0", "0.4, 0, 5, 0.6, . . . ", and the like) are set when a plurality of visual targets having different visual acuity values are presented. Furthermore, the controller 26 can select and set an appropriate visual acuity value based on the eye refractive power measured by the objective examination. By performing the objective measurement in advance in the above-described manner, the ophthalmologic apparatus 10 can efficiently and appropriately perform the subjective examination such as the measurement of the eye refractive power, and the reliability of the subjective examination can be improved. In addition, required visual acuity values (assumed to be normal values) vary depending on whether the subject sees a far point or a near point. Accordingly, the ophthalmologic apparatus 10 or the examiner does not necessarily need to set the same visual acuity value and can set different visual acuity values in the far-point examination, the midpoint examination, and the near-point examination. In addition, in the case of the monocular vision and the binocular vision, the required visual acuity values are different, and thus the ophthalmologic apparatus 10 or the examiner can set different visual acuity values for the monocular examination and the binocular examination.

The examination distance is the distance at which the visual targets are presented. The examination distance is set to a far-point distance (for example, 5 m) for measurement at a far point, a midpoint or intermediate distance (for example, 2 m) for measurement at a midpoint, and a near-point distance (for example, 50 cm, 40 cm, 33 cm, 20 cm, 10 cm, or the like) for measurement at the near point. Note that the examination distance is not an actual distance between the subject and the visual targets, but is an apparent distance created by each visual target projection system 32 as if the visual targets were presented at a position at this distance.

For example, the subjective examination includes a visual acuity examination (eye refractive power examination), a contrast examination, a night examination, a glare examination, a pinhole examination, and a stereoscopic vision examination. The visual targets for performing these examinations include, for example, visual targets for the contrast examination, visual targets for the glare examination, visual targets for the night examination, and visual targets for the stereoscopic vision examination. Each visual target includes, for example, a Landolt ring, a Snellen visual target, an E-chart, a character, a picture, a figure, a photograph, and the like as described above. The enlargement magnification of the visual target is increased as the examination distance becomes closer to the near-point distance so that the subject feels perspective when visually recognizing the visual target with the naked eye. As a display mode of each visual target, for example, a contrast (for example, 100%, 50%, 25%, etc.) is set at the time of the contrast examination. On the other hand, when a normal visual acuity examination is performed, the contrast is set to 100%. In addition, when a plurality of visual targets are presented in the contrast examination, a multi-contrast visual target display mode (see FIG. 6), a single-contrast visual target display mode (see FIG. 7A), an ETDR visual target display mode (see FIG. 7B), and the like are set as display modes. The multi-contrast visual target display mode presents a plurality of visual targets with different contrasts. The single-contrast visual target display mode presents a plurality of visual targets with a single contrast. In the ETDR visual target display mode, the visual acuity values change from the top to the bottom.

In addition, the night examination is performed on the assumption of appearance at night, and a single-contrast visual target display mode (see FIG. 7C) for the night examination is used. In this visual target display mode, the color of the visual targets is reversed to white and the color of the background is reversed to black. In addition, when the glare examination is performed, the contrast of the visual target is set to 100% to perform the glare examination together with the normal visual acuity examination, or the contrast examination and the glare examination may be combined by appropriately setting the contrast in a state where the visual targets of the contrast examination and the visual targets of the night examination are presented. In addition, in a case where the parallax is provided to the subject eyes E in the stereoscopic vision examination for examining how each visual target appears in the binocular vision, the visual target is presented by changing the visual angles to, for example, 30 seconds, 1 minute, 2 minutes, 3 minutes, 4 minutes, or the like.

Here, the contrast examination is an examination for obtaining a spatial frequency characteristic (contrast sensitivity) of the visual system including the subject eyes. The contrast is a difference in luminance (brightness) between the region where the visual target is displayed and the background on the display 32a. The contrast is obtained by following Equation (1).

Equation (1) is as follows:

$$C(\%) = 100 \times (Max - Min)/(Max + Min) \quad (1)$$

In Equation (1), C is contrast, Max is maximum luminance (brightness) of the visual target region or the background, and Min is minimum luminance (brightness) of the visual target region or the background.

Different contrasts result in different appearances of the presented visual target. That is, when the contrast is at a high level (e.g., C=100%), the boundary between the visual target and the background becomes clear, and the visual target appears relatively clear. The lower the contrast to a medium level (e.g., C=50%) or a low level (e.g., C=25%), the less distinct the boundary between the visual target and the background, and the more blurred the visual target appears.

Even in a case where the subject does not feel any difference in the appearance of a visual target in the normal visual acuity examination (i.e., with contrast of 100%) between a condition where the intraocular lens is inserted in the eye and a condition where the intraocular lens is not inserted in the eye, the appearance of the visual target with different contrasts may differ between the two conditions. In addition, the insertion of the intraocular lens may change appearance at night, the reflection and blur of light of a vehicle during night driving, and appearance in the binocular vision. Such a change in appearance also varies depending on the type of intraocular lens and the like. Therefore, it is very important and meaningful to perform the contrast examination, the glare examination, and the stereoscopic vision examination with various contrasts at various examination distances to enable the subject to live a comfortable life (visual life) without having a feeling of strangeness in appearance.

In addition, the controller 26 also functions as a pupil detection portion and a visual axis calculation portion and detects the positions of the bright spot images Br and the pupil centers of the left subject eye EL and the right subject eye ER. Based on the detected positions and pupil centers, the controller 26 calculates the angles formed by the visual axes of the left and right subject eyes EL, ER, and the optical axes L of the left-eye and right-eye measurement heads 16L, 16R. The pupil centers are detected from each of the anterior segment images E' of the left and right subject eyes EL, ER that have been acquired by the imaging elements 31g of the observation systems 31. The positions of the bright spot images Br are detected as the corneal reflections of the left and right subject eyes EL, ER, that is, the images of the bright spots, based on the bright spots obtained by imaging the parallel light flux from the second alignment light sources 36a of the second alignment systems 36 in the left and right subject eyes EL, ER. Each of the bright spot images Br is formed in a spot shape at a predetermined position (half of the curvature radius r of the cornea, r/2) inside the cornea Ec by the incidence of the parallel light flux.

Based on the calculated visual axes (more specifically, angles formed by visual axes and optical axes), the controller 26 can also determine whether the subject eyes E are oblique or squint or whether the subject is appropriately visually fixating the visual target. The controller 26 can also notify the examiner and the subject of the determination result by displaying the determination result on the display 30 or displaying schematic diagrams of the subject eyes E on which the numerical values of the angles and the visual axes are displayed on the display 30. As a result, the examiner and the like can also recognize the presence or absence of heterophoria or squint and the suitability of fixation. Furthermore, the controller 26 can rotate the measurement heads 16 in the X direction based on the calculated visual axes to arrange the measurement heads 16 at positions aligned with the visual axes of the subject eyes E.

Figure 8:
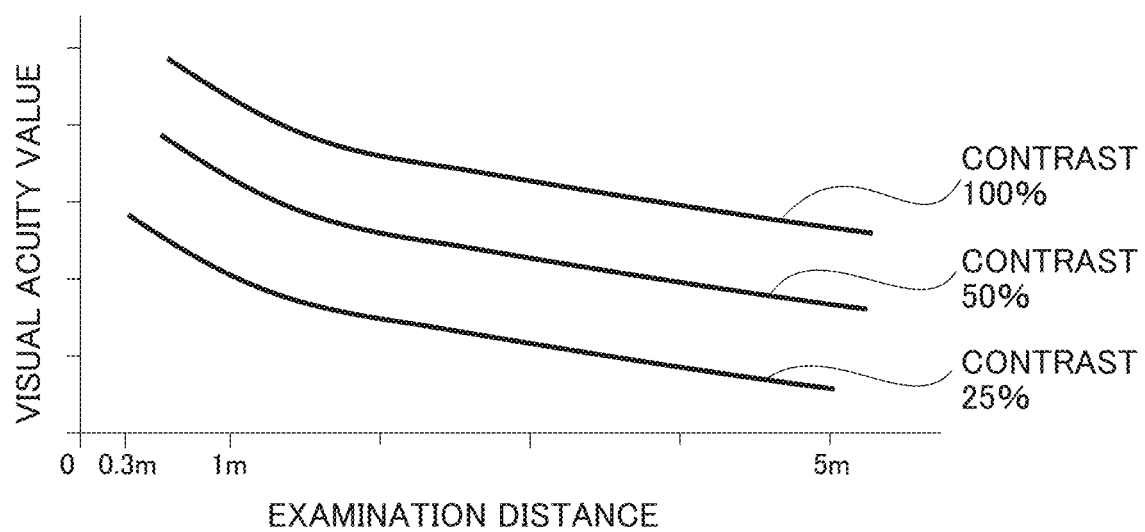
FIG. 8 is a graph of measurement results displayed on a display surface.

Furthermore, the controller 26 also functions as a measurement result output portion. The controller 26 associates the presentation condition of the visual targets presented to the subject with the measurement result of the eye characteristics when the visual targets are presented under the above presentation condition and outputs the associated presentation condition and measurement result to the display 30, a printer, or the like. Specifically, for example, in the case of the contrast examination, as illustrated in FIG. 8, the controller 26 forms a graph showing the relationship among the examination distance, the visual acuity value (measurement result), and the contrast, and controls the display 30 to display the graph on the display surface 30a. Further, the graph is printed by the printer automatically or when a printing instruction is input from the input portion 30b or the like. The graph is not limited to the two-dimensional graph as illustrated in FIG. 8. A three-dimensional graph or the like is also suitable, so that the examiner and the subject more clearly grasp the correlation of the plurality of items.

In addition, the controller 26 controls the display 30 to display the anterior segment images E' of the right and left subject eyes E on the display surface 30a. By the examiner visually recognizing the anterior segment images E', it is possible to recognize whether the examination is appropriately performed. For example, in a case where alignment or examination may not be performed well, the cause or the like can be grasped. Examples of the cause of failure in the alignment and the examination include failure in fixation, failure in binocular vision, squint or heterophoria, ptosis, suppression, pupil constriction, and the inclination of the head. Therefore, by visually recognizing the anterior segment images E' on the display 30, the examiner can clearly grasp the cause of the failure in the alignment or the like. Then, it is possible to quickly take measures by correcting the position of the head or calling the subject's attention, and it is possible to improve the success rate of re-alignment and re-examination.

(Example of Operation of Ophthalmologic Apparatus) An example of the operation of the ophthalmologic apparatus 10 having the above-described configuration according to the present embodiment will be described with reference to the flowchart of FIG. 9. In the flowchart of FIG. 9, a case will be described in which, after the objective examination is performed with binocular vision, the visual acuity examination, the contrast examination, the night examination, and the glare examination are performed as the subjective examination while changing the examination distances. Note that the operation of the ophthalmologic apparatus 10 is not limited to the following steps. In addition, it is also possible to change the order of the examinations and the types of the examinations, and it is also possible to examine the eyes one by one by changing the examination distance and the contrast.

First, in Step S1, the controller 26 drives the left-eye and right-eye X-direction rotation drive portions 24 to rotate the left-eye and right-eye measurement heads 16 in the X direction to set the presentation position of the fixation target at a predetermined position. Next, in Step S2, the visual target projection systems 32 display the fixation target (e.g., point light source visual target) at the center positions of the displays 32a. In this state, the examiner instructs the subject to fixate the fixation target.

In Step S3, the imaging elements 31g of the left-eye and right-eye measurement optical systems 21 start imaging the anterior segments of the left and right subject eyes E under the control of the controller 26. The controller 26 displays, on the display surface 30a, the anterior segment images E' of the left and right subject eyes E in accordance with image signals output from the imaging elements 31g. Furthermore, the controller 26 may display the fixation target currently presented by the displays 32a on the display surface 30a.

When the examiner visually recognizes the anterior segment images E' displayed on the display 30, the examiner can confirm the suitability of fixation, the suitability of binocular vision, squint, heterophoria, ptosis, suppression, pupil constriction, the inclination of the head, and the like. As a result, the examiner can take measures. For example, the examiner opens the subject eyelids by his or her hand for the eyelid droop and calls the subject's attention to the inclination of the head.

In Step S4, under the control of the controller 26, the first alignment systems 35 perform alignment in the Z direction by the above-described operation and the second alignment systems 36 perform alignment in the X direction and the Y direction by the above-described operation in a state where the subject fixates the fixation target.

In Step S5, the eye refractive power measurement system 33 receives (or automatically receives) an instruction input for the objective examination from the input portion 30b by the examiner, and executes the objective examination such as the eye refractive power (refraction) measurement and the corneal shape measurement (keratometry) by the KERATO system 37 under the control of the controller 26.

Next, in Step S6 the controller 26 acquires the examination mode (for example, multifocal IOL mode) in accordance with (or automatically) the instruction input for the subjective examination from the input portion 30b by the examiner and instruction for examination mode selection. In Step S7, the controller 26 acquires the presentation condition according to the examination mode from the storage 29. In addition, the visual acuity value is set according to the degrees of the refractive power of the subject eyes E of the subject based on the eye refractive power or the like acquired in the objective examination in Step S5.

Next, in Step S8, in order to set the visual axes of the subject eyes E to the direction according to the examination distance, the controller 26 drives the left-eye and right-eye X-direction rotation drive portions 24 according to the examination distance to rotate the left-eye and right-eye measurement heads 16 in the X direction. For example, in the case of the examination at the far-point distance, the measurement heads 16 are rotated so as to be oriented as illustrated in FIG. 3A and the visual axes are set to the state of infinity. In Step S9, to present the visual targets at the far-point distance, the controller 26 moves the first focusing lenses 32e to respective predetermined positions. In the case of the examination at the far-point distance, the controller 26 moves the first focusing lenses 32e to far points.

Next, in Step S10, the controller 26 controls the visual target projection system 32 to display the visual targets on the displays 32a at an enlargement magnification corresponding to the type of the visual targets, the display mode, the visual acuity value, and the far-point distance, and display the same visual targets (enlargement magnification may not be the same) on the display surface 30a of the display 30. First, the visual target projection systems 32 present the visual targets with a contrast of 100% to perform the normal visual acuity examination (Step S11).

In a case where each of the visual target projection systems 32 displays a plurality of visual targets having different visual acuity values in a table format, the examiner instructs the subject to verbally respond to the state (for example, the orientation of a Landolt ring) of each visual target in a predetermined row or a predetermined column such that the subject answers how the visual target appears to him or her. Alternatively, the examiner instructs the subject to answer how far identification can be made. The examiner inputs the subject's response by performing an operation such as tapping each visual target identified by the subject on the display surface 30a or clicking or dragging the identified row and/or column on the display surface 30a in accordance with the subject's response. A response signal by the above operation is transmitted from the input portion 30b to the controller 26. In Step S12, the controller 26 obtains position information of the visual target clicked (or tapped, dragged, or the like) in accordance with the response signal, and acquires a measurement result such as a visual acuity value based on the position information. The response may be input from the subject input portion 28a of the subject controller 28 by the subject.

Figure 6:
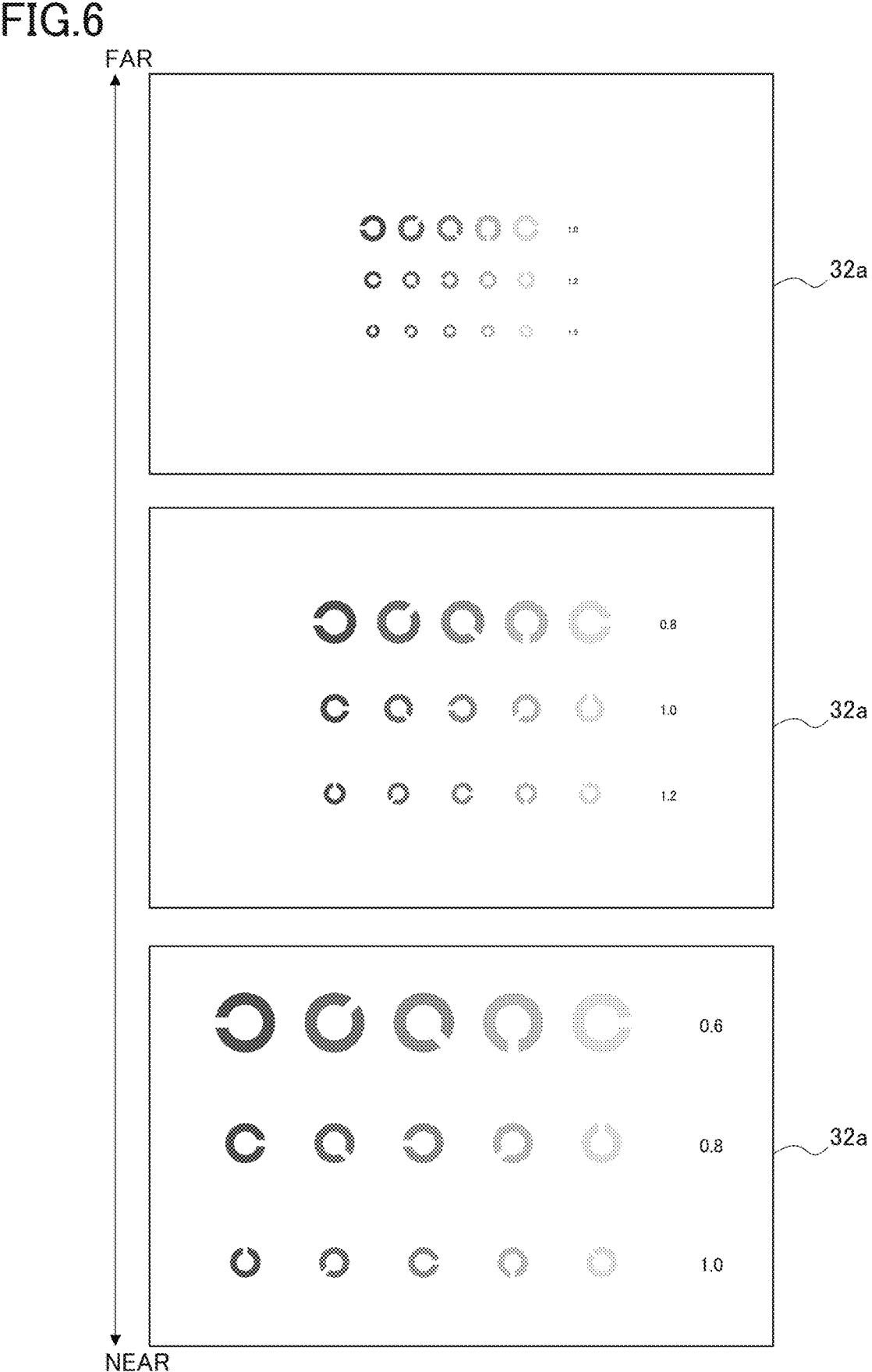
FIG. 6 is a view illustrating an example of visual targets (multi-contrast visual targets) displayed on a display when examination distances are a far-point distance, a midpoint distance, and a near-point distance.
Figure 7A:
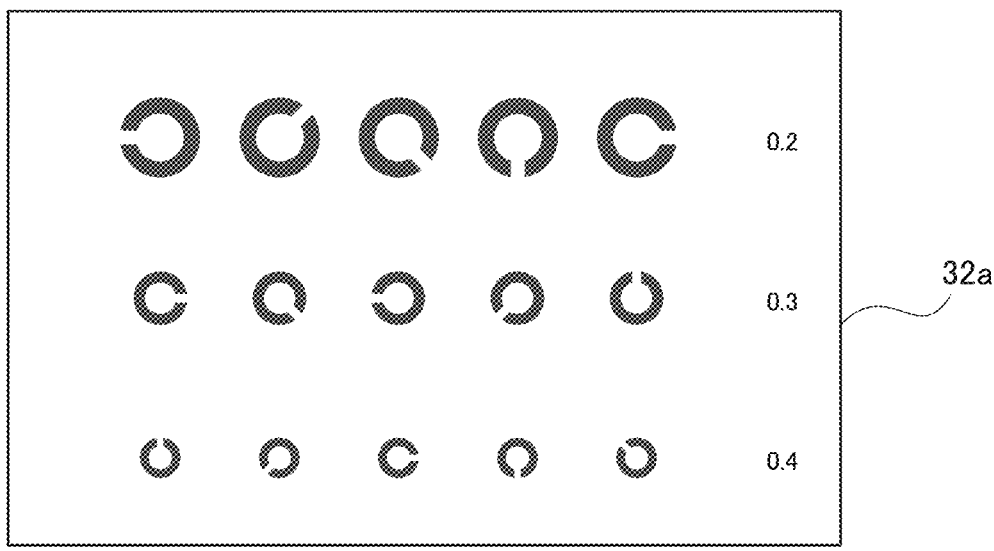
FIG. 7A is a view illustrating single-contrast visual targets that are examples of the visual targets displayed on the display.
Figure 7B:
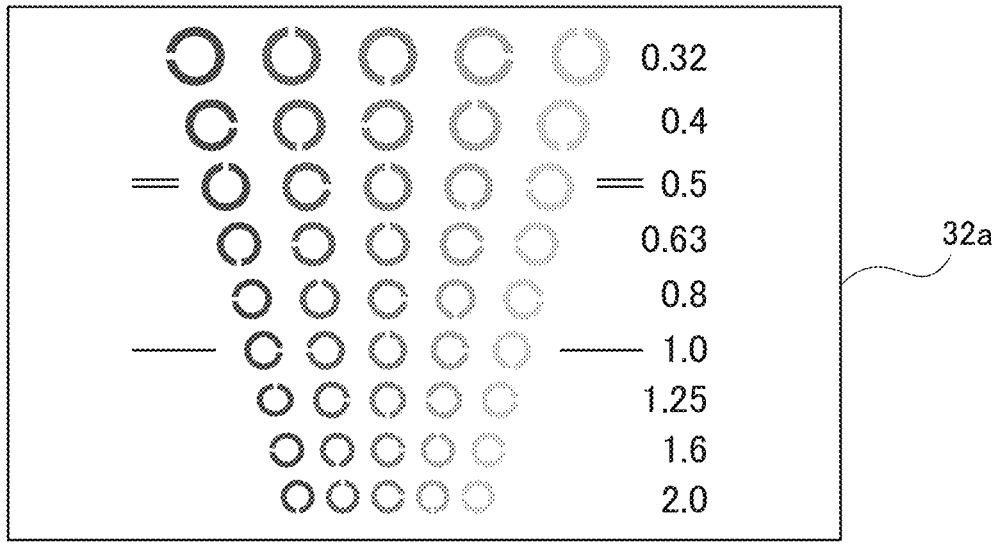
FIG. 7B is a view illustrating ETDR visual targets that are an example of the visual targets displayed on the display.

To perform another type of examination, the ophthalmologic apparatus 10 repeats the processing of Steps S10 to S12 according to the examination to be performed. When the contrast examination is performed, for example, as illustrated in FIG. 6, the controller 26 controls the displays 32a and the display surface 30a to display multi-contrast visual targets in which a contrast varies for each column. The upper diagram of FIG. 6 illustrates visual targets displayed on each of the displays 32a at the time of the examination at the far-point distance. As illustrated in FIG. 6, by simultaneously presenting the visual targets with different visual acuity values and different contrasts at one examination distance and performing an examination, the measurement (examination) can be performed quickly and efficiently and the accuracy of the measurement can be improved.

Figure 7C:
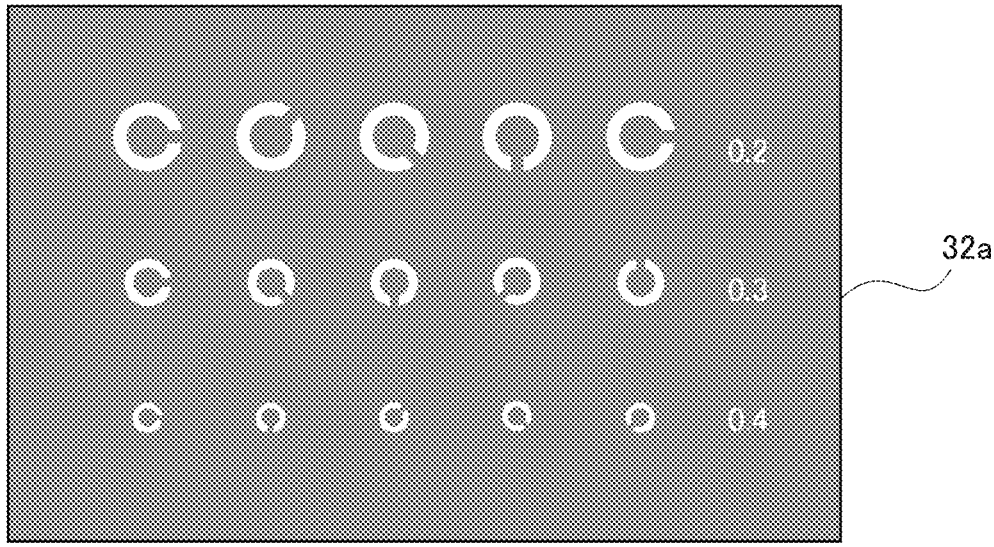
FIG. 7C is a view illustrating single-contrast visual targets for a night examination that are examples of the visual targets displayed on the display.

The controller 26 acquires the measurement result of the contrast examination based on the response signal from the input portion 30b (or the subject input portion 28a). Next, when the night examination is performed, as illustrated in FIG. 7C, the controller 26 controls the displays 32a and the display surface 30a to display, at an enlargement magnification corresponding to the far-point distance, single-contrast visual targets for the night examination in which the color of the visual targets and the color of the background are reversed. Then, the controller 26 acquires the measurement result of the night examination based on the response signal from the input portion 30b. Next, when the glare examination is performed, the controller 26 controls the glare light sources 32k to blink while displaying the single-contrast visual targets or the like for the night examination of FIG. 7C on the display surface 30a and instructs the subject to respond. The controller 26 acquires the measurement result of the glare examination based on the response signal from the input portion 30b.

In the next Step S13, the controller 26 determines whether the measurements at all examination distances have been completed or not. When the measurement has been completed (YES), the program proceeds to Step S14. When the measurement has not been completed yet (NO), the program returns to Step S8 to perform the subjective examination at the next examination distance.

For example, in the case of performing the examination at the midpoint distance, in Step S8, the controller 26 controls the rotation of the measurement heads 16 such that the visual axes are directed to midpoints. Then, in Step S9, the controller 26 moves the first focusing lenses 32e to the midpoints to present the visual targets at the midpoint distance (for example, 2 m). Then, in Step S10, the controller 26 displays the visual targets on the displays 32a or the like at the enlargement magnification corresponding to the midpoint distance (for example, in the case of contrast examination, visual targets illustrated in middle diagram of FIG. 6), and performs the visual acuity examination on the subject. In Step S12, the controller 26 acquires the measurement result based on the response signal from the input portion 30b. The controller 26 repeats the above processes to perform the normal visual acuity examination, the contrast examination, the night examination, the glare examination, and the stereoscopic vision examination at the midpoint distance and acquires measurement results thereof.

In addition, in the case of performing the examination at the near-point distance, in Step S8, the controller 26 controls the rotation of the measurement ds 16 such that the visual axes are directed to the near points. Then, in Step S9, the controller 26 moves the first focusing lenses 32e to the near points to present the visual targets at the near-point distance (for example, 50 cm or the like). Then, in Step S10, the controller 26 displays the visual targets on the displays 32a or the like at an enlargement magnification corresponding to the near-point distance (for example, in the case of contrast examination, visual targets illustrated in lower diagram of FIG. 6), and performs the visual acuity examination on the subject. In Step S12, the controller 26 acquires the measurement result based on the response signal from the input portion 30b. The controller 26 repeats these processes to perform the normal visual acuity examination, the contrast examination, the night examination, the glare examination, and the stereoscopic vision examination at the near-point distance and acquires the measurement results thereof.

When all types of the examinations have been completed at all the examination distances, the program proceeds to Step S14, and the controller 26 graphically displays the measurement results on the display surface 30a and prints the measurement results when a print instruction is given. For example, in the case of the contrast examination, the controller 26 displays a graph as illustrated in FIG. 8. In addition, after this, the objective examination may be performed, so that the examiner also confirms whether the result of the subjective examination is appropriate or not. Thus, the operation of the ophthalmologic apparatus 10 ends.

(Modification) Hereinafter, a modification of the ophthalmologic apparatus 10 according to the present embodiment will be described. An ophthalmologic apparatus 10 according to the modification has the same configuration and functions as those of the ophthalmologic apparatus 10 of the first embodiment illustrated in the figures such as FIG. 1. In the modification, the controller 26 further controls each display 32a such that a mark corresponding to a response operation from the subject input portion 28a is superimposed on visual targets and displayed.

In the ophthalmologic apparatus 10 according to the modification, at the time of the subjective examination, the controller 26 displays visual targets corresponding to the examination mode on the displays 32a (and display surface 30a of examiner controller 27) as illustrated in the left diagrams of FIGS. 10A and 10B. Then, the subject visually recognizes the visual targets displayed on the displays 32a, and responds to individual identifiable visual targets by a tap operation or a click operation from the subject input portion 28a such as a touch panel or a mouse, or responds to an identifiable range by a drag operation, a swipe operation, or the like. The controller 26 receives a response signal in accordance with the response operation from the subject input portion 28a and controls the displays 32a such that a mark or image corresponding to the response operation is superimposed on the visual targets and displayed. In the left diagram of FIG. 10A, a dot (circle) mark indicating the tap operation is displayed, and in the left diagram of FIG. 10B, a line indicating the drag operation is displayed.

The controller 26 acquires the measurement result based on the response operation by the subject, surrounds visual targets in the range that can be identified by the subject with a rectangular mark or image, and displays the visual targets on the displays 32a, as illustrated in the right diagrams of FIGS. 10A and 10B. With this display, the subject can confirm the measurement result. In addition, the mark in accordance with the response operation by the subject and the rectangular mark of the measurement result are also displayed on the display surface 30a of the examiner controller 27, so that the examiner can clearly grasp the response state and the measurement result of the subject.

In addition, when the controller 26 controls to display a cursor, a mark of a finger, or the like on the displays 32a in accordance with the position information of a finger of the subject on the touch panel, the position information of a mouse, or the like, the subject can easily perform a response operation. In addition, a camera or the like may capture an image of the finger of the subject, and the controller 26 may acquire the position information of the finger based on the captured image.

Even with the ophthalmologic apparatus 10 according to the modification as described above, the examination distance and the presentation condition of the visual targets can be changed as desired, and the characteristics of the subject eyes at various examination distances and der various presentation conditions can be quickly and easily measured, thereby improving the measurement efficiency. Furthermore, when the subject performs the response operation using the subject input portion 28a, it is possible to acquire the eye characteristics more efficiently and quickly.

Figure 11A:
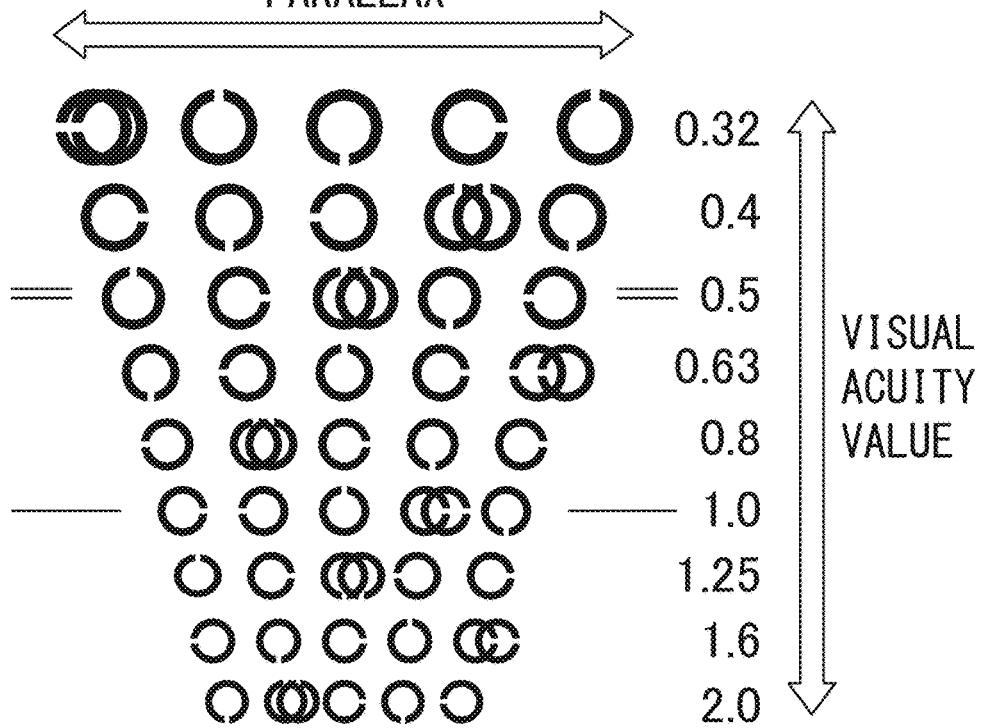
FIG. 11A is a view illustrating ETDR visual targets for a stereoscopic vision test that are examples of visual targets for the stereoscopic vision test.
Figure 11B:
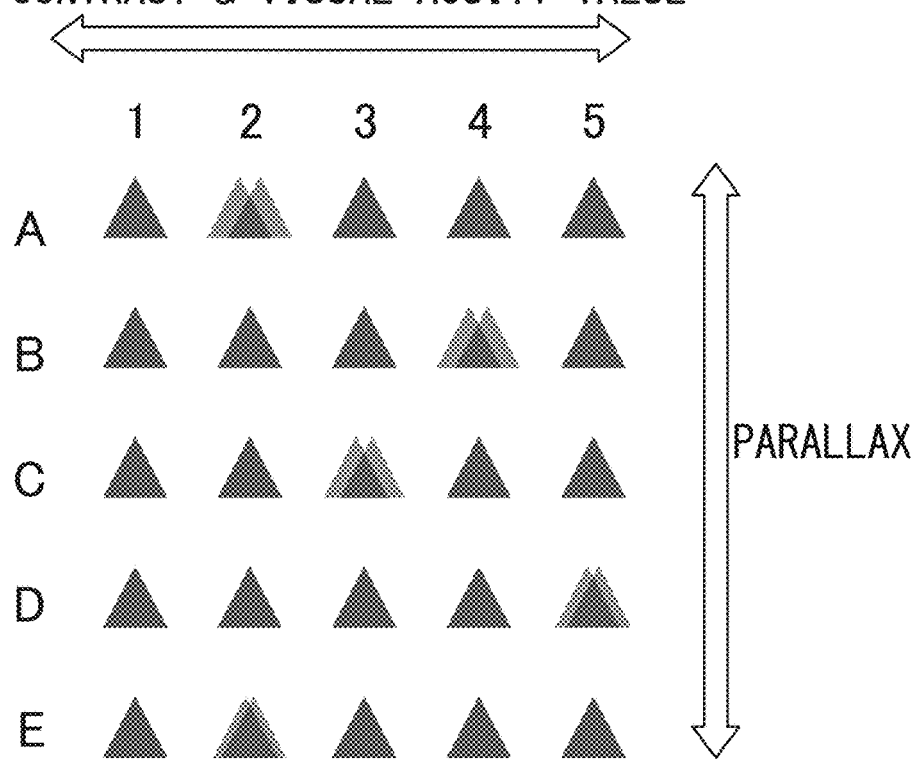
FIG. 11B is a view illustrating visual targets for a precise stereoscopic vision test that are examples of the visual targets for the precise stereoscopic vision test.

In addition, FIGS. 11A and 11B illustrate examples of visual targets for the stereoscopic vision examination that may be used in the ophthalmologic apparatus 10 according to the first embodiment and the modification. FIG. 11A illustrates an example of ETDR visual targets for the stereoscopic vision examination in which the vertical axis represents a visual acuity value and the horizontal axis represents a parallax. FIG. 11B illustrates an example of visual targets for a precise stereoscopic vision examination in which the vertical axis represents the parallax, and the horizontal axis represents a contrast and a visual acuity value (fixed value).

In the example of FIG. 11A, for example, the visual target projection systems 32 of the ophthalmologic apparatus 10 set visual angles to 30 seconds, 1 minute, 2 minutes, 3 minutes, and 4 minutes from the left side of the figure, and display the visual targets with the corresponding parallax applied to one of five visual targets in each row. In the example of FIG. 11B, the contrast and the visual acuity value are constant, and for example, the visual target projection systems 32 set visual angles to 30 seconds, 1 minute, 2 minutes, 3 minutes, and 4 minutes from the bottom of the figure, and display the visual targets with the corresponding parallax applied to one of five visual targets in each row. When the stereoscopic vision examination is performed using the visual targets illustrated in FIGS. 11A and 11B, the eye refractive power and the like are measured in advance by the objective examination, and the ophthalmologic apparatus 10 or the examiner sets the visual acuity values and the like of the visual targets based on the measurement result, so that the subjective examination can be performed more appropriately and quickly.

In addition, when such visual targets for the stereoscopic vision examination are displayed, the position P at which the visual targets are presented, that is, the examination position can be set to a desired distance by rotating the left-eye and right-eye measurement heads 16 to change the rotational angles α. The subject operates the subject input portion 28a to respond to the visual targets that appear stereoscopically projected among the displayed visual targets. The controller 26 acquires the measurement result in accordance with the response signal based on the response operation.

Note that the visual targets illustrated in FIGS. 11A and 11B indicate images in which the visual targets presented to the left and right subject eyes E are superimposed, and the actual visual targets are separately displayed on the displays 32a of the measurement heads 16 for each of the left eye and the right eye. As an example, FIG. 12 illustrates a display example of the visual targets for the precise stereoscopic vision examination of FIG. 11B on the displays 32a for the left and right eyes. The left diagram in FIG. 12 illustrates a display example of the visual targets on the display 32a for the left eye, and the right diagram of FIG. 12 illustrates a display example of the visual targets on the display 32a for the right eye. In addition, in each diagram of FIG. 12, other visual targets that provide the parallax relative to the visual targets are indicated by phantom lines to facilitate understanding. Furthermore, in the left diagram in FIG. 12, a centerline representing the centers of the visual targets on the left-eye display 32a is indicated by a phantom line in a column "2". For example, the visual targets for providing the parallax, such as visual targets of "A2" and "E2", are displayed at positions shifted from the centerline.

In addition, by displaying the superimposed images of the visual targets illustrated in FIGS. 11A and 11B on the display 30 of the examiner controller 27, for example, the examiner can easily recognize the state of the visual targets and the parallax presented to the subject.

Figure 13:
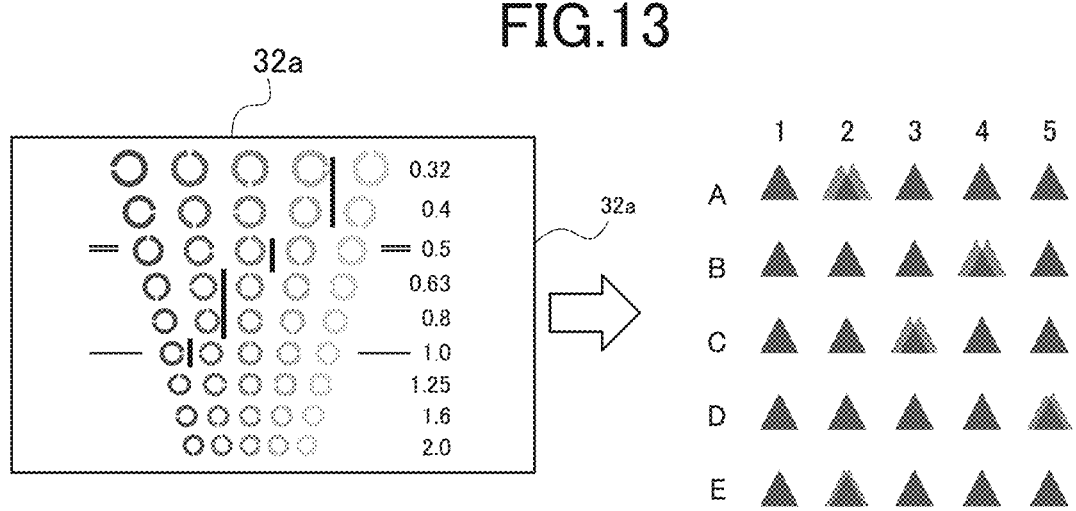
FIG. 13 is a view illustrating an example of an examination using the multi-contrast visual targets and the visual targets for the precise stereoscopic vision test.

Next, an example of the subjective examination using a plurality of visual targets will be described with reference to FIG. 13. FIG. 13 illustrates an example of an examination using the multi-contrast visual targets and the visual targets for the precise stereoscopic vision examination that are illustrated in FIGS. 11B and 12. First, the controller 26 displays, on the displays 32a, the multi-contrast visual targets illustrated in the left diagram of FIG. 13. The subject operates the subject input portion 28a to respond to the identifiable visual targets.

Next, the controller 26 displays, on the left and right displays 32a, the visual targets for the precise stereoscopic vision examination (see FIG. 12) corresponding to the right diagram of FIG. 13 with a predetermined contrast and a predetermined visual acuity value in accordance with the result of the measurement using the multi-contrast visual targets. For example, in a case where visual targets with the contrast of 50% can be identified with the visual acuity value of 0.32 in the examination using the multi-contrast visual targets, the controller 26 changes the parallax with the above contrast and the visual acuity value and displays 25 stereoscopic visual targets on the left and right displays 32a. Therefore, it is not necessary for the examiner or the like to manually select or input the visual acuity value and the contrast, and the next stereoscopic vision examination can be immediately performed.

Then, the subject uses the subject input portion 28a to select visual targets that appear to be stereoscopically projected and performs a response operation. The controller 26 controls to display the measurement result based on the response operation on the displays 32a or the display 30 of the examiner controller 27. Next, based on the previous measurement result, the stereoscopic visual targets with a changed visual acuity value and a changed contrast are displayed, and the examination can be repeated. Note that the visual targets and the measurement procedure described with reference to FIG. 13 are examples, and the present disclosure is not limited thereto. For example, it may be possible to examine the visual acuity value and the parallax (stereoscopic vision) using the ETDR visual targets for the stereoscopic vision examination that are illustrated in FIG. 11A, and perform, based on the measurement result, a more detailed stereoscopic vision examination using the visual targets for the precise stereoscopic vision examination that are illustrated in FIG. 11B. In addition, the controller 26 controls to graphically display the measurement result on the display surface 30a and to print the result when a print instruction is given.

Figure 14:
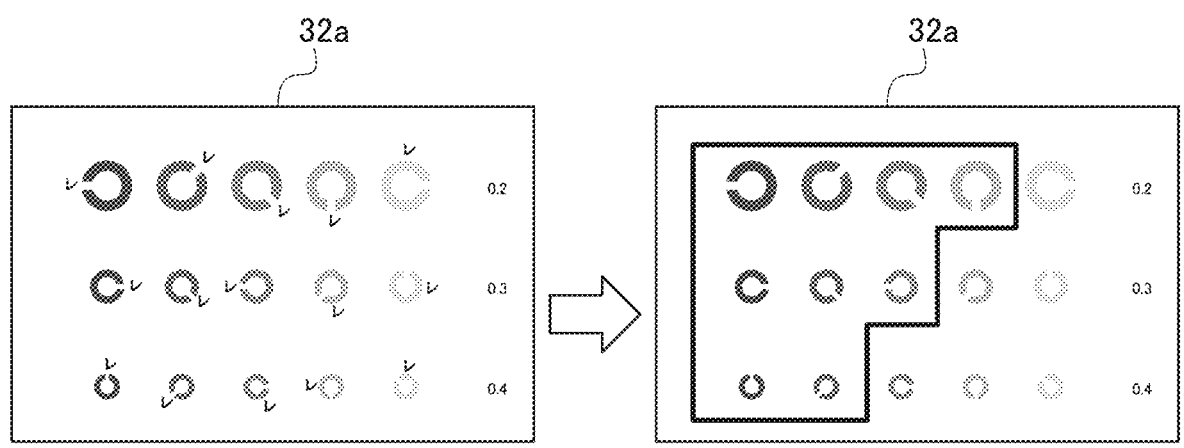
FIG. 14 is a view illustrating another modification in which a controller determines whether a response input from a subject input portion is correct or incorrect, the view illustrating a state in which the subject responds by a tap operation and a state in which a measurement result in accordance with the correct or incorrect response is displayed.

In addition, as described with reference to FIGS. 10A and 10B, in the self-reporting method in which the subject responds to identified visual targets, the reliability of the response may be an issue, which may affect the measurement result. In order to avoid this, another modification will be described. In this modification, the controller 26 is configured to determine whether the response of the subject in the subjective examination is correct or incorrect. Specifically, as illustrated in the left diagram of FIG. 14, the controller 26 displays visual targets corresponding to the examination mode on the displays 32a (and display surface 30a of examiner controller 27). In the example of FIG. 14, multi-contrast visual targets that include Landolt rings are displayed. The subject performs the response operation by tapping the vicinity of the opening of each Landolt ring on the display 32a. In the left diagram of FIG. 14, positions tapped by the subject are indicated with checkmarks, but markers indicating the tapped positions may be superimposed on the visual targets and displayed. In addition, the subject may perform the response operation by indicating the direction of the opening of the ring with a joystick or the like. In addition, the examiner may perform the response operation through the input portion 30b of the examiner controller 27 in response to the verbal response of the subject.

Then, the controller 26 determines whether the response of the subject is correct or incorrect based on response signals from the subject input portion 28a and/or the input portion 30b, and acquires the measurement result based on the determination result. As a result, in the subjective examination, the reliability of the response of the subject is improved, and more objective and more accurate measurement results can be obtained. Furthermore, the controller 26 may refer to the measurement result in the objective measurement to determine whether the response is correct or incorrect. In addition, the controller 26 may be configured to surround only visual targets identified correctly by the subject with a rectangular mark and display the visual targets with the rectangular mark on the displays 32a as illustrated in the right diagram of FIG. 14. Thereby, the subject and the examiner can easily confirm the result of determining whether the response is correct or incorrect and the measurement result.

Second Embodiment

Hereinafter, an ophthalmologic apparatus 10 according to a second embodiment and a measurement method using the ophthalmologic apparatus 10 will be described. The ophthalmologic apparatus 10 according to the second embodiment has a basic configuration (hardware and functional configurations) similar to the ophthalmologic apparatus 10 of the first embodiment illustrated in FIGS. 1 to 5. However, the measurement method (measurement program) performed by the controller 26 is different from that of the first embodiment. Further, in the ophthalmologic apparatus 10 according to the second embodiment, a "prescription mode" can be set as an examination mode in addition to the examination modes described in the first embodiment. In the prescription mode, the examination is performed by changing the examination distance to an optional examination distance.

Figure 15:
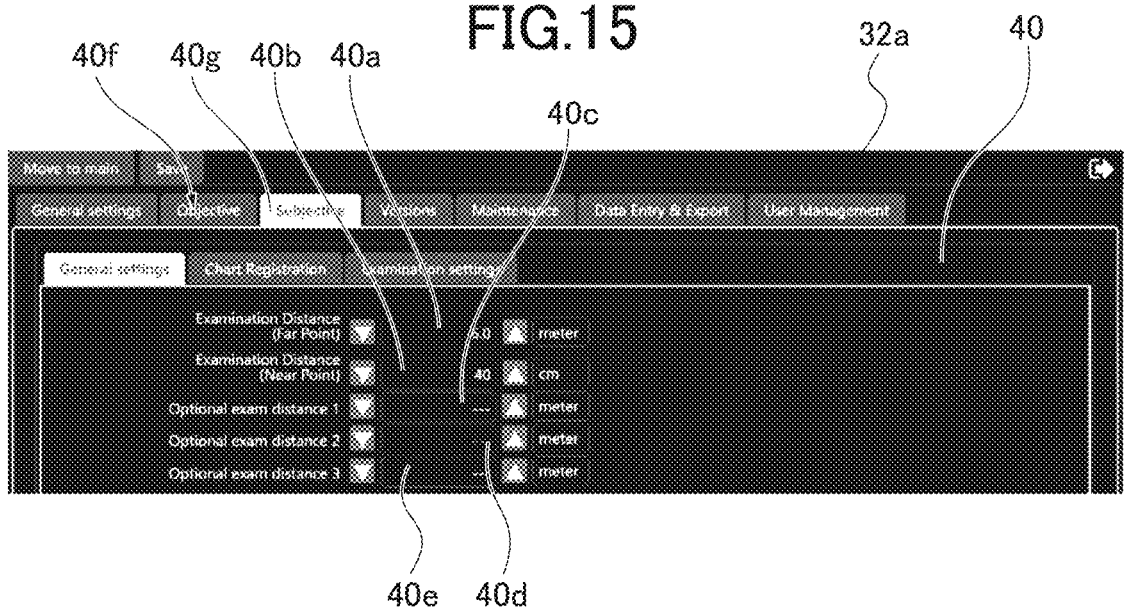
FIG. 15 is a view illustrating an ophthalmologic apparatus according to another embodiment of the present disclosure, the view illustrating an example of a setting screen for various parameters.
Figure 16A:
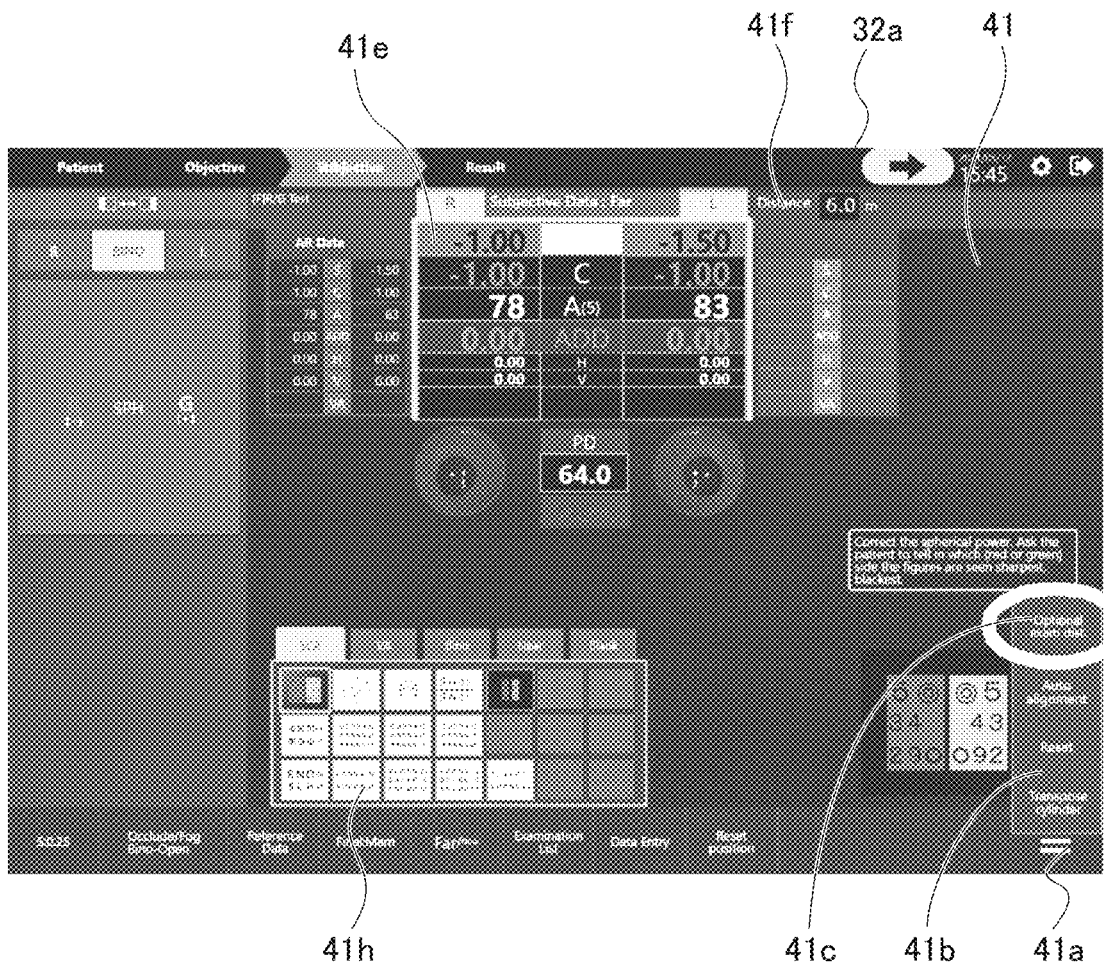
FIG. 16A is a view illustrating an ophthalmologic apparatus according to another embodiment of the present disclosure, the view illustrating an example of a subjective examination screen before changing an examination distance to an optional examination distance.
Figure 16B:
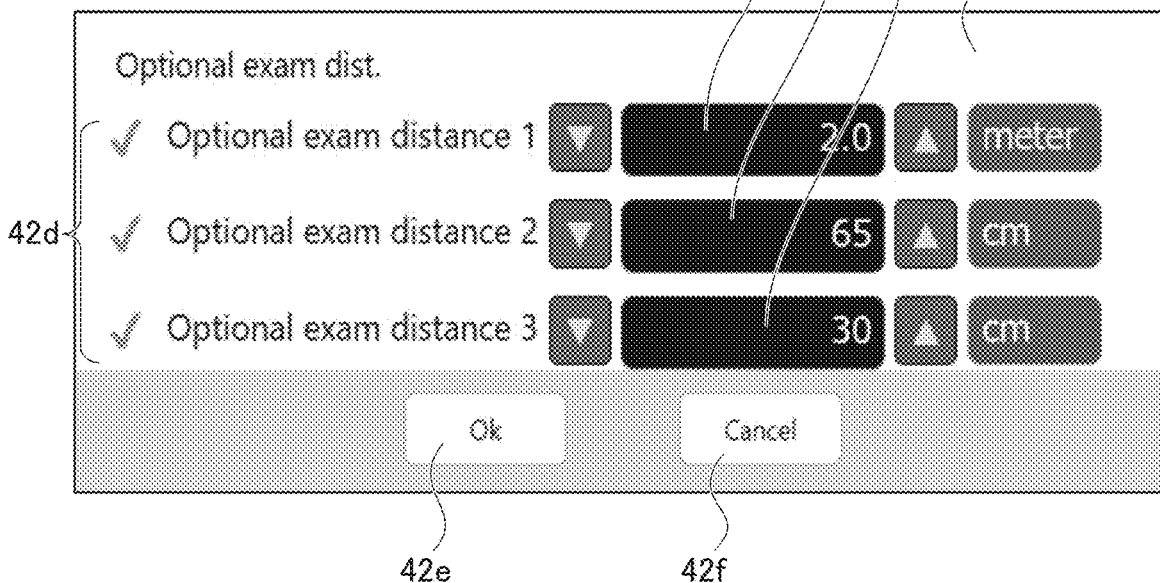
FIG. 16B is a view illustrating an ophthalmologic apparatus according to another embodiment of the present disclosure, the view illustrating an example of a window for setting the optional examination distance.
Figure 17:
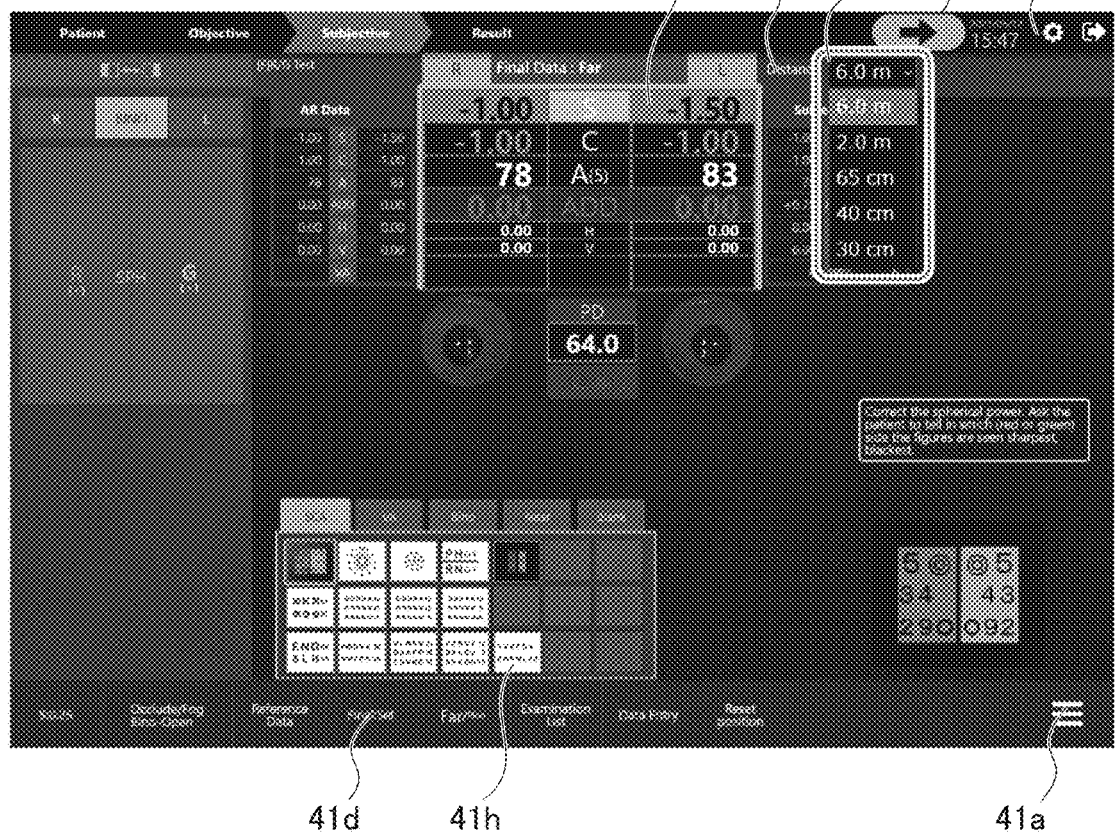
FIG. 17 is a view illustrating an ophthalmologic apparatus according to another embodiment of the present disclosure, the view illustrating an example of a subjective examination screen in which an examination distance is changed to an optional examination distance.

Hereinafter, checking the visual acuity with the optional examination distance will be described as an example of a measurement method performed by the ophthalmologic apparatus 10 with reference to FIGS. 15 to 18B. FIGS. 15 to 17 illustrate examples of images displayed on the display surface 30a of the display 30 of the examiner controller 27. FIG. 15 illustrates a setting screen 40 for various parameters. FIG. 16A illustrates a subjective examination screen 41 before switched to the optional examination distance. FIG. 16B illustrates a window 42 for setting the optional examination distances. FIG. 17 illustrates the subjective examination screen 41 after switched to the optional examination distance. The input portion 30b, which is a touchscreen or a touch panel, is provided on the display surface 30a of the display 30, so that the user such as the examiner can input values, instructions, or the like via the input portion 30b. FIGS. 18A and 18B illustrate output samples of measurement results.

The "optional examination distance" indicates a third examination distance that is selected and set by the user as desired in addition to a first examination distance (far-point) for the basic far-point examination and a second examination distance (near-point) for the near-point examination. Hereinafter, the first examination distance for the far-point examination is referred to as a "far-point examination distance" and the second examination distance for the near-point examination is referred to as a "near-point examination distance". As illustrated in FIG. 15, in the present embodiment, the user can select, on the setting screen 40, at least one (e.g., three) examination distance as the optional examination distance (third examination distance). In the present embodiment, an examination distance equal to or more than 1.0 m is used as the far-point examination distance (far) and displayed on the display surface 30a with a unit "m". On the other hand, an examination distance less than 1.0 m is used as the near-point examination distance (near) and displayed on the display surface 30a with a unit "cm".

FIG. 15 illustrates the setting screen 40 when a "Subjective" bar 40g from menu bars 40f is touched, tapped, or clicked. The setting screen 40 includes a far-point examination distance area 40a, a near-point examination distance area 40b, a first optional examination distance area 40c, a second optional examination distance area 40d, and a third optional examination distance area 40e. The user can register the three optional examination distances in addition to the far-point examination distance and the near-point examination distance.

The user can register below-listed set values to the first to third optional examination distances areas 40c to 40e. Note that a sign "–" listed below means "not-set" and the sign "–" is set to the first to third optional examination distance areas 40c to 40e as a default set value (default) at the time of shipping. The controller 26 stores, in the storage 29, the optional examination distances set by the examiner. The set values are as follows. In the case that the unit is "meter", the set values are "–, 6.0, 5.5, 5.0, 4.5, 4.0, 3.5, 3.0, 2.5, 2.0, 1.5, 1.0". In the case that the unit is "cm", the set values are "–, 95, 90, 85, 80, 75, 70, 65, 60, 55, 50, 45, 40, 35, 33, 30, 25". In the case that the unit is "feet", the set values are "–, 20, 19, 18, 17, 16, 15, 14, 13, 12, 11, 10, 9, 8, 7, 6, 5, 4, 3". In the case that the unit is "inch", the set values are "–, 34, 32, 30, 28, 26, 24, 22, 20, 18, 16, 14, 13, 12, 10".

(Checking Visual Acuity with Optional Examination Distance) Hereinafter, a procedure for the examiner to examine the visual acuity of the subject at the optional examination distance will be described. After objectively measuring the visual acuity of the subject by the objective examination, the examiner changes the examination to the subjective examination. After that, the examiner performs the subjective examinations at the normal far-point examination distance and the near-point examination distance and then performs the subjective examination at the optional examination distance to prescribe for correction of the subject eye E.

In the present embodiment, the examiner sets the examination distance in the range of 6 m to 25 cm (20 feet to 10 inches) to perform the subjective examination at the optional examination distances. By utilizing this function, the ophthalmologic apparatus 10 of the present embodiment can adjust the spherical power of the subject and record or store the visual acuity values at the three optional examination distances in addition to the examinations at the basic "far-point examination distance (far)" and "the near-point examination distance (near)". Hereinafter, a procedure for changing the optional examination distances will be described.

(Changing Optional Examination Distances on Subjective Examination Screen) The user can change the optional examination distance for each subject during the subjective examination at the default "optional examination distance" (Optional exam distance) set on the setting screen 40. In order to perform the examination for another subject next, the changed "optional examination distance" is being applied until the screen returns to the subject information input screen not shown).

FIG. 16A illustrates an example of the subjective examination screen 41. In a main data area 41e of the subjective examination screen 41, refractive correction values (refractive data) currently set to each portion or component of the measurement heads 16 and the measured visual acuity values (these values are referred to as "main data" hereinafter) are displayed. For example, the spherical power (S), the cylindrical power (C), the cylinder axis (A), the addition power (ADD) of the subject eyes E, and the like are displayed. When the examination is changed from the objective examination to the subjective examination, the values obtained by the objective examination are set to the main data area 41e.

In the subjective examination, the user can increase and decrease these values by touching or tapping the display surface 30a (input portion 30). However, some values may not be changed depending on the examination distances. Table 1 below shows whether each value for each examination distance can be changed or not and the holding (storing) state thereof. Changing the values shown with "*" in Table 1 changes the values at all of the examination distances.

The examiner changes the optional examination distances on the subjective examination screen 41 by the following procedure. (1) First, when the examiner touches or taps a hamburger menu 41a on the subjective examination screen 41, the controller 26 displays a menu 41b on the subjective examination screen 41. (2) The examiner touches or taps an "optional examination distance setting" (Optional exam dist) button 41c from the displayed menu 41b. (3) Upon receiving this input operation, the controller 26 displays the window 42 for setting the "optional examination distances" (Optional exam dist) as illustrated in FIG. 16B.

The examiner changes the three optional examination distances (optional examination distances 1, 2, 3) by changing values in first, second, third optional examination distances change areas 42a, 42b 42c of the window 42. In the example illustrated in FIG. 16B, the examiner has set 2.0 m of the far-point examination distance shorter than 5.0 m of the normal far-point examination distance for the optional examination distance 1. The examiner has also set 65 cm for the optional examination distance 2, which is longer than 40 cm of the normal near-point examination distance. Further, the examiner has set 30 cm for the optional examination distance 3, which is shorter than 40 cm.

A reference numeral 42d in FIG. 16B denotes marks indicating whether or not changes can be made (referred to as changeability mark 42d hereinafter). The user can change the optional examination distances with checkmarks. On the other hand, the user cannot change the optional examination distances without the checkmarks (or with "x" marks, or the like). This is because the controller 26 prevents the optional examination distance from being changed while the examination at this optional examination distance is currently being performed. When the examination at the optional examination distance is not being performed, the controller 26 adds and displays the checkmarks of the changeability marks 42d such that all of the optional examination distances can be changed.

(4) After the optional examination distances are changed, the examiner touches or taps an OK button (OK) 42. With this input operation, the controller 26 stores the changed optional examination distances in the storage 29 and closes the window 42. Thereby, the changes of the optional examination distances are completed.

TABLE 1

|  | SPHERICAL POWER S | CYLINDRICAL POWER C | CYLINDER AXIS A | PRISM VALUE P | ADDITION POWER ADD | VISUAL ACUITY VALUE VA |
|---|---|---|---|---|---|---|
| FAR-POINT EXAMINATION DISTANCE | HELD BY DISTANCE | COMMON* | COMMON* | HELD AS FAR-POINT VALUE | — | HELD BY DISTANCE |
| NEAR-POINT EXAMINATION DISTANCE | — (UNCHANGEABLE) | COMMON | COMMON | HELD AS NEAR-POINT VALUE | HELD BY DISTANCE | HELD BY DISTANCE |
| OPTIONAL EXAMINATION DISTANCE (FAR-POINT EXAMINATION DISTANCE) | HELD BY DISTANCE | COMMON | COMMON | UNCHANGEABLE (FAR-POINT VALUE) | — | HELD BY DISTANCE |
| OPTIONAL EXAMINATION DISTANCE (NEAR-POINT EXAMINATION DISTANCE) | — (UNCHANGEABLE) | COMMON | COMMON | UNCHANGEABLE (NEAR-POINT VALUE) | HELD BY DISTANCE | HELD BY DISTANCE |

(5) On the other hand, when the examiner does not change the optional examination distances, the examiner touches or taps a cancel button (Cancel) 42f. With this input operation, the controller 26 does not store the unchanged optional examination distances in the storage 29 and closes the window 42.

As described above, the optional examination distances can be changed during the subjective examination. Accordingly, when the examination measurement result at the optional examination distance is stored in the middle of the subjective examination and this optional examination distance is changed, the controller 26 does not store the measurement result at this examination distance in the storage 29 but deletes or discards the result.

(Changing to Optional Examination Distance) Changing to the optional examination distance can be performed when the measurement mode is the "prescription mode". Specifically, it is necessary for the measurement mode to be set to the "prescription mode" when the examination is to be performed at the optional examination distance by changing the examination distance to the optional examination distance set on the screen illustrated in FIG. 15 or FIG. 16B. The "prescription mode" is a mode for correcting each correction value measured by the subjective examination, making an actual prescription, and recording (storing) it. The obtained "prescription data" is stored as the prescription. The examiner changes the examination distance to the optional examination distance and performs the measurement by the following procedure.

(1) The examiner touches or taps the "Prescription: Set" (Final: Set) button (or "Prescription: Record" (Final: Mem) button) 41d among the function buttons which are located at the bottom of the subjective examination screen 41. If there is any prescription record, "Prescription: Set" is displayed as the button 41d. On the other hand, if there is no prescription record, "Prescription: Record" is displayed as the button 41d. With this operation, the controller 26 switches the main data of the main data area 41e to the prescription data (recorded prescription).

(2) The examiner touches or taps the "Test distance display/change area" button 41f located in the upper of the subjective examination screen 41 (see FIG. 16A). With this operation, the controller 26 displays an "examination distance list" 41g, which is a list of the examination distances to be changed, on the subjective examination screen 41 as illustrated in FIG. 17.

(3) The examiner selects the optional examination distance to which the examiner wants to change the examination distance from the displayed examination distances in the "examination distance list" 41g. With this selection operation, the controller 26 executes processes from Step S8 to Step S10 illustrated in FIG. 9 in accordance with the selected optional examination distance similar to the first embodiment. Specifically, in order to orient the visual axes of the subject eyes E in accordance with the examination distance, the controller 26 drives the left-eye and right-eye X-direction rotation drive portions 24 in accordance with the examination distance to rotate the left-eye and right-eye measurement heads 16 in the X direction (Step S8) and moves the first focusing lenses 32e to a position in accordance with the examination distance (Step S9). Then, the controller 26 controls the visual target projection system 32, displays the visual targets on the displays 32a under the presentation condition such as the enlargement magnification in accordance with the examination distance, and also displays the same visual targets on the display surface 30a of the display 30 (Steps S10, S11). (4) Thereby, the subject can perform the examination at the selected optional examination distance. By receiving the response and the like from the subject or the like, the controller 26 analyzes the response and the like and acquires the measurement results such as the visual acuity value (Step S12).

After the subjective examinations at all of the optional examination distances selected by the examiner have been completed, the controller 26 displays a list and/or graph of the measurement results on the display surface 30a and prints the measurement results in response to a printing instruction from the examiner (Step S14).

FIGS. 18A and 18B illustrate output samples of the measurement results. FIG. 18A illustrates the output sample printed on a rolled thermal paper. FIG. 18B illustrates the output sample printed on A4 paper. In these output samples, the spherical powers (spherical power) and the visual acuity values (visual acuity) measured at the normal far-point examination distance, the near-point examination distance, and the first to third optional examination distances are printed for each of the examination distances. The measurement results at the normal far-point examination distance (first examination distance), the near-point examination distance (second examination distance), and the first to third optional examination distances (third examination distance) are printed as Test distance 1 to Test distance 5 in order of the examination distance length. Note that in the example illustrated in FIGS. 18A and 18B, the "spherical powers" that are measured at each of the examination distances are output but the output is not limited thereto. Instead of the spherical powers measured at each of the examination distances or in addition thereto, differences and/or the addition power with respect to the spherical power at the first examination distance may be printed, for example.

Hereinafter, in the measurement method according to the present embodiment, what can be measured at the optional examination distances will be explained. After the refractive correction has been determined with the basic far-point examination distance or the near-point examination distance ("Exam Distance (Far Point)"/"Exam Distance (Near Point)"), the measurement at the optional examination distance can be used for checking following items: whether the sufficient visual acuity is obtained when the subject looks at the target at other examination distance: and the spherical power needed to obtain the sufficient visual acuity.

Accordingly, it is possible to adjust the spherical powers (spherical power) and store the visual acuity value (visual acuity) during the examination at the optional examination distance. In addition, the controller 26 allows the input operation by the examiner such that the examiner can change the cylinder power and the cylinder axis (cylinder power/cylinder axis) in the main data area 41e during the examination at the optional examination distance. However, since these values are used as common values for other examination distances, the controller 26 restricts the input operation by the examiner such that the values of the cylinder power and the cylinder axis that have been changed at the optional examination distance are not changed in the main data area 41e even the examination distance is changed.

Also, the subjective examination includes a phoria examination and a binocular function examination (phoria test/binocular function test) that examine appearance in the binocular vision. In the present embodiment, these examinations can be performed at all examination distances, that is the normal far-point examination distance (first examination distance), the near-point examination distance (second examination distance), and the optional examination distances (third optional examination distance). The controller 26 displays the prism values obtained by these examinations for the examination distances and stores them in the storage 29. The phoria examination and the binocular function examination may not be necessarily performed at the optional examination distance. When these examinations are not performed at the optional examination distance, the controller 26 displays the prism value measured at the far-point examination distance or the near-point examination distance as the prism value of the optional examination distance and stores it in the storage 29.

The reasons for the above specification are as follows. Even if the phoria examination and the binocular function examination are performed at the various examination distances, in the case that making the prescription for the lenses of the bifocal glasses and/or the multifocal IOL, the prism amount that can be prescribed for these lenses is limited to one. Also, since the convergence of the subject eyes E changes depending on the examination distance, the correspondence between the convergence and the examination distance becomes complicated. For the above reasons, it is less necessary to perform the phoria examination and the binocular function examination at the optional examination distance. Not performing these examinations simplifies and clarifies the examination distances and the examination efficiency.

Also, for the same reasons, the controller 26 may restrict the input operation by the user during the examinations at the optional examination distances such that the phoria examination and the binocular function examination cannot be performed. At this time, with regard to charts (visual targets) within a chart page 41h (see FIG. 17, etc.), the controller 26 also restricts the input operation by the user such that the examiner cannot select the charts registered for the phoria examination and the binocular function examination.

In addition, as described above, the user such as the examiner can set the optional examination distance in the range of 6.0 m to 25 cm (20 feet to 10 inches). The controller 26 uses a predetermined distance, for example, the examination distance equal to or more than 1.0 m (equal to or more than threshold) is used as the far-point examination distance (far) and the examination distance less than 1.0 m (less than threshold) is used as the near-point examination distance (near) and performs setting of the presentation condition for the visual target, and the like. Then, when the examination distances are changed, in the case of changing one far-point distance to another far-point distance and one near-point distance to another near-point distance, the examination conditions and the charts (visual targets) being used are inherited. In the case of crossing the threshold of the far-point and near-point distances, the charts (visual targets) are not inherited but the controller 26 controls the portions or components of the ophthalmologic apparatus 10 such that the visual acuity examination is automatically performed with the charts (visual targets) in accordance with the examination distance.

Next, the refractive power displayed in the main data area 41e during the examination at the optional examination distance will be described. In the case that the optional examination distance is the far-point examination distance (far), the values displayed in the "addition" ("ADD") of the main data area 41e are values obtained by subtracting the spherical power (current spherical power set on the measurement head) currently set to the measurement heads 16 from the near-point spherical power ("Exam Distance (Near Point)"(=spherical power of examination distance (far-point)+addition power of examination distance (near-point)) (=Spherical power of "Exam Distance (Far Point)"+ADD of "Exam Distance (Near Point)").

In other words, the controller 26 displays, in the "addition" ("ADD") of the main data area 41e the addition power ADD2 calculated by following Equation (2). In Equation (2), ADD2 is the addition power at the optional examination distance (third examination distance), S1 is the spherical power at the far-point examination distance (far examination distance, first examination distance), ADD1 is the addition power at the near-point examination distance (near examination distance, second examination distance), and S2 is the spherical power (spherical power currently set to measurement heads 16) at the optional examination distance (third examination distance).

Equation (2) is as follows:

$$ADD2 = S1 + ADD1 - S2 \qquad (2)$$

On the other hand, during the examination at the optional examination distance which is the near-point distance (near), the controller 26 displays, in the "spherical power" ("S") in the main data area 41e, the far-point examination distance (far) (Exam Distance (Far Point)), that is the far-point spherical power measured at the first examination distance and displays, in the "addition" ("ADD"), the optional examination distance (third examination distance), that is a value obtained by subtracting the spherical power displayed in the "spherical power" ("S") from the spherical power currently set to the measurement heads 16.

In the subjective examination, there is a cross cylinder test as one of astigmatism (R/G) tests. In the cross cylinder test, the refractive power is applied in a predetermined direction with respect to the astigmatism test visual target to present it to the subject eyes E. During the cross cylinder test, it may be desirable to maintain an equivalent spherical power by adjusting the spherical powers at all of the examination distances.

In the present embodiment, the user can set on the setting screen 40 whether to maintain the equivalent spherical power or not. In the case of setting to maintain the equivalent spherical power (i.e., ON setting), every time the user changes the cylindrical power during the cross cylinder test, the controller 26 changes or adjusts the spherical power to maintain the equivalent spherical power and displays it on the display surface 30a. The change or adjustment of the spherical power is also applied to the examination at the optional examination distance. Maintaining the equivalent spherical power means that the value of S+C/2 is kept constant by adjusting the spherical power S and/or the cylindrical power C during the examination or test at a predetermined examination distance.

The ophthalmologic apparatus of the present disclosure has been described with reference to the first and second embodiments and modifications. The specific configurations of the ophthalmologic apparatus are not limited to ones described in the embodiments and modifications and numerous modifications and additions may be made to the present disclosure without departing from its scope as defined in the appended claims.

The ophthalmologic apparatus 10 according to the first and second embodiments and modifications has the configuration in which the measurement optical system 21 includes the observation system 31, the visual target projection system 32, the subjective examination system 34, the first alignment system 35, the second alignment system 36, the eye refractive power measurement system 33 and the keratometry (KERATO) system 37 which are objective measurement optical system. However, the ophthalmologic apparatus of the present disclosure is not limited to the above configuration. For example, an ophthalmologic apparatus disclosed in U.S. Pat. No. 7,775,662 (the disclosure of which is hereby incorporated by reference in its entirety) is another example of the ophthalmologic apparatus that can be used for the present disclosure. This ophthalmologic apparatus includes a plurality of optical members that are disposed between the subject eyes E and the visual target projection system and correct the visual function of the subject eyes, an optometry optical system (phoropter) that selectively place each of the optical members between the subject eyes and the visual target projection system, and a visual target presentation device. In such an ophthalmologic apparatus, as disclosed in the present disclosure, the visual target presentation device changes the presentation condition such as the examination distance to display the visual targets and thereby, the adjustment of the spherical power and storing or recording of the visual acuity value can be performed at the three optional examination distances in addition to the examinations at the basic far-point examination distance (far) and the near-point examination distance (near). Thereby, the examination distances and the presentation conditions of the visual targets can be changed as desired, and the characteristics of the subject eyes are quickly and easily measured at the various examination distances under the various presentation conditions, thereby improving measurement efficiency.

What is claimed is:

1. An ophthalmologic apparatus comprising:
a visual target projection system that is configured to present a visual target to a subject eye under a presentation condition; and
a controller,
wherein:
the controller is configured to control the visual target projection system to present the visual target at a first examination distance for a far-point examination of the subject eye, a second examination distance for a near-point examination of the subject eye, and a third examination distance that is different from the first examination distance and the second examination distance;
the visual target projection system comprises a focusing lens; and
the visual target projection system is configured to change the examination distance from the presentation position of the visual target to the subject eye among the first examination distance, the second examination distance and the third examination distance by moving the focusing lens forward and backward along an optical axis.

2. The ophthalmologic apparatus according to claim 1, wherein the third examination distance is one of plural third examination distances that are different from each other and set in advance.

3. The ophthalmologic apparatus according to claim 1, further comprising:
an input portion that is configured to receive an input operation from a user,
wherein the controller is further configured to:
acquire a measurement result based on the input operation through the input portion;
store, as the measurement result in the far-point examination, the measurement result that is obtained at a distance equal to or more than a threshold; and
store, as the measurement result in the near-point examination, the measurement result that is obtained at a distance less than the threshold.

4. The ophthalmologic apparatus according to claim 1, wherein the visual target is one of plural visual targets, and the controller is further configured to control the visual target projection system to present, at the third examination distance: (i) a first of the visual targets for measuring a spherical power of the subject eye; (ii) a second of the visual targets for measuring a cylindrical power of the subject eye; and (iii) a third of the visual targets for measuring a cylinder axis of the subject eye.

5. The ophthalmologic apparatus according to claim 1, further comprising:
an input portion that is configured to receive an input of a correction value for correcting a visual function of the subject eye comprising a spherical power, a cylindrical power, and a cylinder axis; and
a display that is configured to display the correction value,
wherein the controller is further configured to control the visual target projection system to display, on the display, the correction value input from the input portion, and present the visual target under the presentation condition corresponding to the correction value.

6. The ophthalmologic apparatus according to claim 5, wherein the controller is further configured to display, as the correction value of the spherical power, an addition power with respect to the correction value of the spherical power that is input at the first examination distance on the display when the visual target is presented at the third examination distance and the third examination distance is for the near-point examination.

7. The ophthalmologic apparatus according to claim 5, wherein;
the controller is further configured to display an addition power (ADD2) on the display when the visual target is presented at the third examination distance and the third examination distance is for the far-point examination;
the addition power (ADD2) is calculated by ADD2=S1+ADD1−S2; and
ADD2 is the addition power at the third examination distance, S1 is a spherical power at the first examination distance, ADD1 is an addition power at the second examination distance, and S2 is a spherical power at the third examination distance.

8. The ophthalmologic apparatus according to claim 5, wherein the controller is further configured to change the spherical power and display the changed spherical power on the display to maintain an equivalent spherical power upon receiving the input of the correction value of the cylindrical power from the input portion when the visual target is presented for the far-point examination.

9. The ophthalmologic apparatus according to claim 1, further comprising:
an objective measurement optical system that is configured to measure characteristics of the subject eye;
wherein the controller is further configured to control the visual target projection system to present the visual target at each of the first examination distance, the second examination distance and the third examination distance based on a measurement result in the objective measurement optical system.

10. The ophthalmologic apparatus according to claim 1, further comprising:

plural optical members that are configured to be placed between the subject eye and the visual target projection system and correct a visual function of the subject eye; and an optometry optical system that is configured to selectively place each of the optical members between the subject eye and the visual target projection system.

11. A measurement method using the ophthalmologic apparatus according to claim 1, the measurement method comprising:

presenting the visual target to the subject eye at the first examination distance by the visual target projection system under control of the controller;

presenting the visual target to the subject eye at the second examination distance by the visual target projection system under the control of the controller; and presenting the visual target to the subject eye at the third examination distance by the visual target projection system under the control of the controller.

* * * * *